(12) United States Patent
Sahiholnasab et al.

(10) Patent No.: US 10,271,753 B1
(45) Date of Patent: Apr. 30, 2019

(54) ELECTROCARDIOGRAPHIC SIGNAL MONITORING DEVICE AND METHOD

(71) Applicant: Medical Wearable Solutions Ltd., Richmond (CA)

(72) Inventors: Vahid Sahiholnasab, Richmond (CA); Edmond Zahedi, North Vancouver (CA); Mohamadtaghi Katanbaf Nezhad, Richmond (CA); Hossein Sahiholnasab, Richmond (CA)

(73) Assignee: Medical Wearable Solutions Ltd., Richmond, CA (US)

( * ) Notice: Subject to any disclaimer, the term of this patent is extended or adjusted under 35 U.S.C. 154(b) by 0 days.

(21) Appl. No.: 15/982,874

(22) Filed: May 17, 2018

Related U.S. Application Data

(60) Provisional application No. 62/643,086, filed on Mar. 14, 2018.

(51) Int. Cl.
| | |
|---|---|
| *A61B 5/0402* | (2006.01) |
| *A61B 5/0424* | (2006.01) |
| *A61B 5/0408* | (2006.01) |
| *A61B 5/0432* | (2006.01) |
| *A61B 5/044* | (2006.01) |
| *A61B 5/00* | (2006.01) |
| A61B 5/04 | (2006.01) |

(52) U.S. Cl.
CPC .......... *A61B 5/0408* (2013.01); *A61B 5/044* (2013.01); *A61B 5/0432* (2013.01); *A61B 5/7232* (2013.01); *A61B 5/0006* (2013.01); *A61B 5/04012* (2013.01); *A61B 5/7203* (2013.01); *A61B 5/7225* (2013.01); *A61B 5/7235* (2013.01)

(58) Field of Classification Search
None
See application file for complete search history.

(56) References Cited

U.S. PATENT DOCUMENTS

| | | | |
|---|---|---|---|
| 3,662,745 A | 5/1972 | Cosentino | |
| 6,306,100 B1 * | 10/2001 | Prass ................... | A61B 5/0488 128/908 |
| 7,338,443 B1 * | 3/2008 | Tucker ................. | G06F 19/327 600/300 |
| 7,558,622 B2 * | 7/2009 | Tran ..................... | A61B 5/0022 600/509 |
| 8,332,019 B2 | 12/2012 | Shimuta et al. | |

(Continued)

FOREIGN PATENT DOCUMENTS

| | | |
|---|---|---|
| WO | 2009074928 A1 | 6/2009 |
| WO | 2017125081 A1 | 7/2017 |

(Continued)

*Primary Examiner* — Brian T Gedeon
(74) *Attorney, Agent, or Firm* — Oyen Wiggs Green & Mutala LLP

(57) ABSTRACT

A device for detecting, monitoring and optionally recording ECG signals is disclosed. The device has at least two electrodes and an on-board memory. The electrodes can be recoatable and/or replaceable. The device can be charged wirelessly through the electrodes or by an internal energy harvesting system. A power saving mode is provided whereby the electrodes are activated by a pre-defined tapping pattern of electrical contact applied by a user and, upon activation, the device starts pairing with and transmitting ECG signals to a receiving station, e.g. a computer, a smart phone, a tablet or the like.

17 Claims, 12 Drawing Sheets

(56) References Cited

U.S. PATENT DOCUMENTS

| | | |
|---|---|---|
| 8,509,882 B2 | 8/2013 | Albert et al. |
| 8,882,667 B2 | 11/2014 | Kim et al. |
| 8,968,195 B2 | 3/2015 | Tran |
| 9,204,814 B2 * | 12/2015 | Baxi .................. A61B 5/04085 |
| 9,439,575 B2 | 9/2016 | Carrara |
| 9,579,060 B1 | 2/2017 | Lisy et al. |
| 9,883,022 B2 * | 1/2018 | Barnes .................... H04L 51/20 |
| 2009/0182205 A1 * | 7/2009 | Cho ..................... A61B 5/0404 |
| | | 600/301 |
| 2015/0057512 A1 | 2/2015 | Kapoor |
| 2015/0297134 A1 | 10/2015 | Albert et al. |
| 2015/0366518 A1 | 12/2015 | Sampson |
| 2016/0066808 A1 * | 3/2016 | Hijazi ................ A61B 5/04085 |
| | | 600/382 |
| 2016/0256063 A1 * | 9/2016 | Friedman ........... A61B 5/04011 |
| 2018/0008158 A1 | 1/2018 | Pekander et al. |

FOREIGN PATENT DOCUMENTS

| | | |
|---|---|---|
| WO | 2017146616 A1 | 8/2017 |
| WO | 2017200420 A1 | 11/2017 |
| WO | 2018013920 A1 | 1/2018 |

* cited by examiner

ELECTROCARDIOGRAPHIC SIGNAL MONITORING DEVICE AND METHOD

REFERENCE TO RELATED APPLICATIONS

This application claims the benefit of U.S. provisional patent application No. 62/643,086 filed 14 Mar. 2018, the entirety of which is incorporated by reference herein for all purposes.

TECHNICAL FIELD

Some embodiments of the present invention relate to an electrocardiographic signal monitoring and/or recording device. The present disclosure relates to a wearable device for monitoring and/or recording electrocardiographic signals and methods of monitoring and/or and recording electrocardiographic signals.

BACKGROUND

Electrocardiographic (ECG) signals are used to measure the electrical activity of human heart, and thereby determine whether the heart is working normally. It can be challenging to accurately record ECG data, especially during infrequent heart episodes. For example, a user may not have access to a reliable ECG monitoring or recording device when and where a heart episode occurs.

There is a general desire for an improved ECG signal monitoring and/or recording device. There is a general desire for a wearable system that detects and records ECG signals. There is further a desire for a wearable system that provides for the obtention of high quality ECG waveforms.

There is further a need for improved ECG signal monitoring and/or recording devices that are portable and can be used independent of any base station or separate control device, including being able to store an ECG waveform independently of any base station or separate control device.

There is further a need for ECG signal monitoring and/or recording devices that can be easily activated by a user, to allow for power to be conserved when the device is not in use by a user, and which can be readily recharged by a user or which is capable of self-charging.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a system for monitoring and recording ECG signals is provided. The system has a housing defining a compartment, at least two electrodes secured to the housing for obtaining ECG signals from a user, a processing unit positioned within the compartment for receiving the ECG signals, a data storage unit positioned within the compartment for storing data based on the ECG signals, a power storage unit positioned within the compartment for supplying power to the system, and a wireless communication unit associated with the housing for communicating the ECG signals or data based on the ECG signals to a receiving device. In some aspects, the data storage unit has a circular memory. In some aspects, the system can output an indication that the circular memory is full, and/or the system is adapted to receive an indication from a user that data in the circular memory should be overwritten.

In one aspect, the system has a charging system for charging the power storage unit. In some aspects, the charging system is a mechanical energy harvesting system. In some aspects, the charging system is a capacitive charging system, and the at least two electrodes are configured to carry out capacitive charging.

In some aspects, the system has an ultra-low power circuit (ULPC) positioned within the compartment, and the ultra-low power circuit is configured to detect the application of a predefined tapping pattern of electrical contact on the at least two electrodes and to supply power to the wireless communication unit upon detection of the predefined tapping pattern.

In some aspects, the electrodes are silver-silver chloride electrodes. In some aspects, the silver-silver chloride electrodes are recoatable. In some aspects, the electrodes are detachable from the housing.

In some aspects, the housing is the arm of a pair of eyeglasses.

In another aspect, a pair of eyeglasses for monitoring and recording ECG signals is provided. The eyeglasses have a first arm and a second arm, a compartment defined within the first arm, a pair of electrodes mounted to the first arm for obtaining ECG signals from a user, a processing unit positioned within the compartment for receiving the ECG signals, a data storage unit positioned within the compartment for storing data based on the ECG signals, a wireless communication unit associated with the first arm for communicating the ECG signals or the data based on the ECG signals to a receiving device, and a power storage unit positioned within the compartment for supplying power to the processing unit, the data storage unit, and the wireless communication unit.

In another aspect, a method of acquiring ECG data using a remote ECG monitoring and data storage system is provided. ECG signals are received from at least two electrodes when a finger from a first hand of a user is placed in contact with a first one of the at least two electrodes and a finger from a second hand of a user is placed in contact with a second one of the at least two electrodes. The received ECG signals are processed using an on-board processing unit provided within a compartment defined by a housing of the remote ECG monitoring and data storage system to yield ECG data. The ECG data are stored in a circular memory provided within the compartment. In some aspects, the step of processing the received ECG signals using the on-board processing unit includes analyzing the ECG signals in both the time and frequency domains, for example to classify the type of ECG abnormality; using a low pass filter to limit the system bandwidth; and/or using notch filtering to remove powerline interference picked up by the electrodes. In some aspects, the step of processing the received ECG signals using the on-board processing unit includes using a data compression scheme to compress the ECG data.

In some aspects, ECG data is transmitted to a receiving device using a wireless transmission protocol. In some aspects, the step of transmitting the ECG data to the receiving device is initiated by application of a predetermined tapping pattern on the at least two electrodes by a user. In some aspects, the step of storing the ECG data in the circular memory includes evaluating whether the circular memory is full and, if the circular memory is full, requesting an indication from a user to proceed before overwriting a record of ECG data previously stored in the circular memory.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The inventors have now developed a device and a method for detecting, monitoring and optionally recording ECG signals. In one example embodiment, the device has at least two electrodes, which can be used to measure ECG signals. In some embodiments, the electrodes are silver-silver chloride electrodes that can be recoated with chloride ions so that they provide reusability and the possibility for long-term use. In some embodiments, the electrodes are removable from the device so that they can be replaced or recoated and reused. In some embodiments, a power storage unit of the device is rechargeable. In some embodiments, the device can be rechargeable via a charging system. The charging system can be a capacitive charging system, a solar cell, a sound/ultrasound wave charge or a movement charger, e.g. an onboard energy harvesting unit. In some embodiments, the capacitive charging system can use the electrodes of the device to carry out recharging of the power storage unit. In some embodiments, a power saving mode is provided whereby the electrodes are activated by a pre-defined tapping pattern of electrical contact applied by a user and, upon activation, the device starts pairing with a receiving device and transmitting ECG signals to the receiving device, e.g. a computer, a smart phone, a tablet or the like. In some embodiments, the device is a wearable unit, e.g. eyeglasses.

As used in this specification, the term "pairing" refers to the process of establishing a wireless connection between two devices using a predefined communication protocol. Each one of the two devices that is paired independently may or may not be connected to other devices or to a network.

Figure 1:
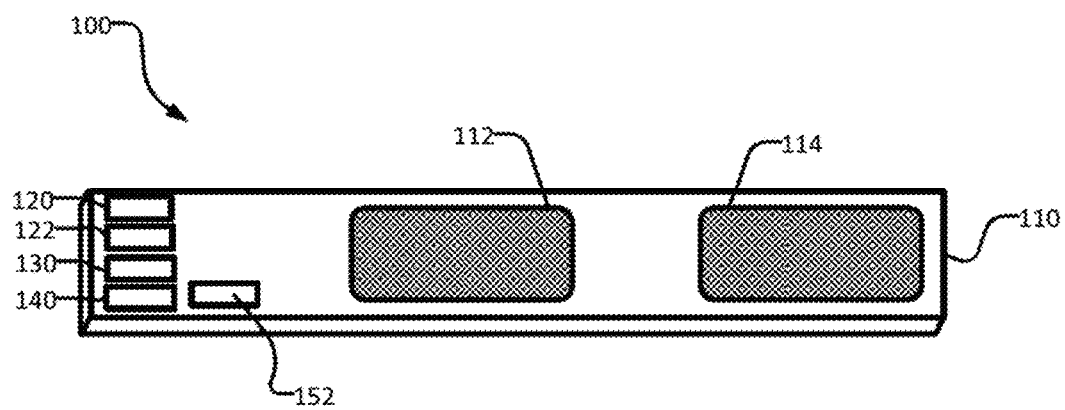
FIG. 1 shows schematically a perspective view of a device for monitoring and/or recording ECG signals according to one embodiment of the present disclosure.

With reference to FIG. 1, an example embodiment of a remote ECG monitoring and data storage system 100 is shown. Remote ECG monitoring and data storage system 100 has a housing 110 and two electrodes 112, 114 embedded in housing 110. Remote ECG monitoring and data storage system 100 is also provided with an on-board data storage unit 120, a data processing unit 122, a wireless transceiver 130, and a power storage unit 140. In some embodiments, wireless transceiver 130 includes both a wireless transmitter and a wireless receiver.

In some embodiments, wireless transceiver is omitted and a port for connecting a cable between system 100 and a receiving device 200 as described below to carry out wired communication between system 100 and receiving device 200 is provided in housing 110. In some embodiments, both wireless transceiver 130 and a port for connecting a cable are provided in system 100, so that a user may choose to have system 100 communicate with receiving device 200 by either wired or wireless modes of communication.

Electrodes 112, 114 are configured to be placed in direct contact with the skin of a user and establish a stable electrical contact therewith. For example, in use of remote ECG monitoring and data storage system 100, a user contacts his or her right and left-hand finger tips to a respective one of electrodes 112, 114, so that a differential electric voltage can be picked up by first electrode 112 through a first finger of the user (e.g. a left finger), through the user's heart, and through the user's second finger (e.g. a right finger) to second electrode 114, thereby providing an ECG signal.

In one example embodiment, a user applies his or her left index finger to first electrode 112 and his or her right index finger to second electrode 114 to use remote ECG monitoring and data storage system 100 to generate the ECG signals to be transmitted and/or recorded and stored via remote ECG monitoring and data storage system 100. In alternative embodiments, any suitable portion of the user's body could be contacted to electrodes 112, 114, so long as the two parts of the user's body that contact each of electrodes 112, 114 are chosen so that an electric current can pass from one of electrodes 112, 114, through a user's heart, and to the other one of electrodes 112, 114.

Without being bound by theory, it is believed that the selection of finger tips over other sites on the body for detecting ECG signals via system 100 has certain advantages, including at least that Finger tips are conveniently accessible parts of the body as they are seldom covered during daily activities.

Because finger tips can be cleaned and dried easily, the issue of poor electrical contact can be easily addressed and therefore contamination on the body is unlikely to affect signal quality of the ECG.

Electrodes 112, 114 can be any suitable electrodes that can be used to measure ECG signals. For example, electrodes 112, 114 can be silver-silver chloride electrodes, stainless steel electrodes or polymer-based electrodes. In some embodiments, the electrodes used are dry electrodes, e.g. would be used by a user with dry hands, for example in embodiments in which the electrodes are stainless steel electrodes. In some embodiments, the electrodes are used by a user having wet fingers, for example by the user applying water, saliva or appropriate electrolytic gel to the fingertips, for example in embodiments in which the electrodes are silver-silver chloride electrodes. Without being bound by theory, silver-silver chloride electrodes may pick up stronger ECG signals from wet hands, and stainless-steel electrodes may pick up stronger and more stable ECG signals from dry hands. In embodiments in which a wetting mechanism is used, the electrical impedance of the electrodes can be decreased, for example by at least one order of magnitude. The reduction in electrical impedance can result in less electrical noise pickup and therefore yield a higher quality signal.

Without being bound by theory, the use of silver-silver chloride electrodes as electrodes 112, 114 may enhance pickup of the ECG signals due to their physical properties. One such physical property is that silver-silver chloride electrodes show a stable half-cell electrical potential that is not significantly affected by the interaction between the skin and the electrode. A differential amplifier can be used to eliminate this steady voltage difference, and any small residual offset electrical potential, i.e. DC offset, can be removed by a high-pass filter. Additionally, there may be less motion artifacts and baseline wandering in the signal.

Figure 2A:
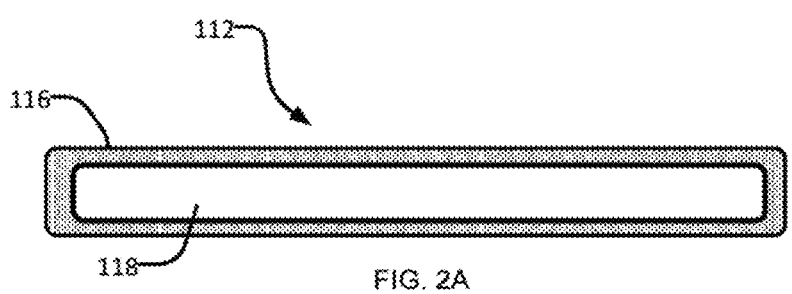
FIG. 2A shows a cross sectional view of an example embodiment of an electrode.
Figure 2B:
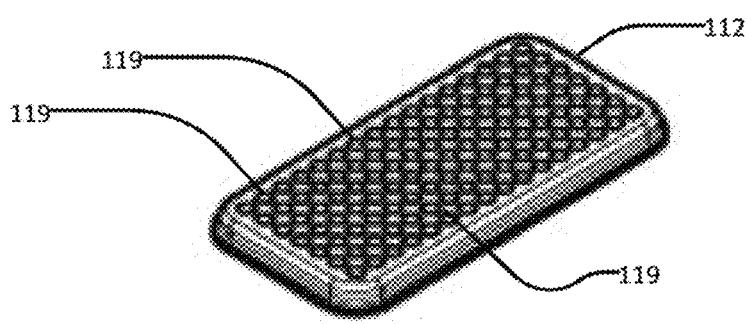
FIG. 2B shows a perspective view of an example embodiment of an electrode.

Electrodes 112, 114 are produced in any suitable manner, e.g. by coating a mixture of silver and silver chloride 116 onto a substrate 118 by dipping, spraying, painting, electrolytic deposition, or the like in embodiments in which silver-silver chloride electrodes are used. As shown in FIGS. 2A and 2B, a silver substrate 118 can be coated with a silver-silver chloride mixture 116 to form the electrode, e.g. as illustrated for electrode 112.

In the illustrated embodiment of FIG. 2B, the surface of electrodes 112, 114, is provided with a plurality of indentations 119. Without being bound by theory, indentations 119 may increase the surface area of electrodes 112, 114 available for contact with fingers of a user and/or provide a tactile feedback sensation to a user, e.g. In embodiments in which the housing 110 of system 100 is smooth, so that the user knows when his or her fingers are in contact with electrodes 112, 114.

Figure 3:
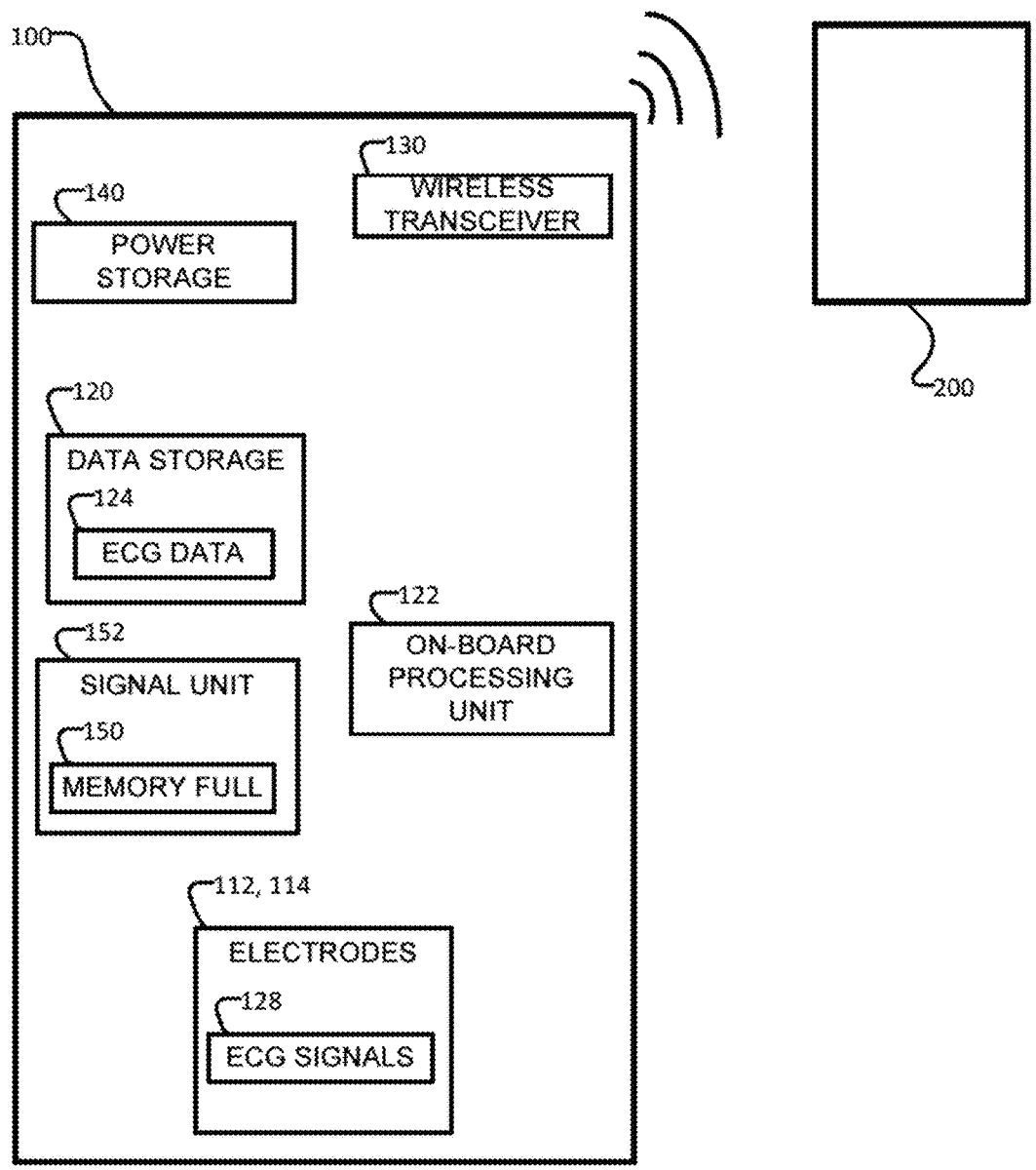
FIG. 3 shows a block diagram of an example embodiment of a remote ECG monitoring and data storage system paired with a base station or receiving device, e.g. a mobile device.

FIG. 3 shows schematically a block diagram of the components of remote ECG monitoring and data storage system 100. In the illustrated embodiment, remote ECG monitoring and data storage system 100 includes a transmission unit to allow it to be placed in wireless communication with a receiving device 200, e.g. a smart phone, a computer, a tablet or any other device that is capable of receiving, processing, displaying, and storing ECG signals and/or ECG data. However, remote ECG monitoring and data storage system 100 is configured so that it can be used to obtain and record ECG signals independently of whether it is paired with a receiving device 200.

The ECG signals 128 that are produced using electrodes 112, 114 when a user contacts his or her fingers therewith as described above are passed to on-board processing unit 122 for processing to yield ECG data 124. ECG data 124 can be stored, for example, in on-board data storage unit 120 as illustrated in FIG. 3, or can be transmitted directly to receiving device 200, as described in greater detail below.

Any desired type of data processing can be carried out by on-board processing unit 122. In some embodiments, on-board processing unit 122 can carry out either or both of analog and digital signal processing.

In some embodiments, on-board processing unit 122 compresses the ECG signals 128 prior to storing ECG data 124. In some embodiments, on-board processing unit 122 analyzes the ECG signals 128 in both the time and frequency domains, for example to classify the type of ECG abnormality. In some embodiments, on-board processing unit 122 has a low pass filter that limits the system bandwidth, thereby minimizing band noise. In some embodiments, on-board processing unit 122 carries out notch flitering for removing any powerline interference picked up by electrodes 112, 114. In one example embodiment, the notch filter is able to remove powerline interference at 60 Hz or 50 Hz.

On-board processing unit 122 can then pass the resultant ECG data 124 on to either or both of on-board data storage unit 120 and wireless transceiver 130, depending on whether remote ECG monitoring and data storage system 100 is in communication with (i.e. paired with) a receiving device 200 or not. In some embodiments, ECG data 124 is initially stored in on-board data storage unit 120, and then at a later time when system 100 is paired with a receiving device 200, ECG data 124 is transferred from on-board data storage unit 120 to an application program operating on the receiving device 200.

The ECG waveform data 124 can be further analyzed by receiving device 200. In some embodiments, further processing of ECG waveform data 124 is carried out by device 200. In some embodiments, processing is carried out in the time domain, frequency domain, and joint time-frequency domain. In some embodiments, the processing used by receiving device 200 are more complex as compared with the processing algorithms used by on-board processing unit 122. In some embodiments, receiving device 200 carries out wavelet transforms and/or uses adaptive filters. In some embodiments, receiving 200 uses deterministic, statistic and/or data driven models to modify the processed ECG signals. In some embodiments, such models are used to compensate for effects caused by variables including for example position and temperature, which could affect ECG signal 128 detected by electrodes 112, 114.

In the illustrated embodiment of remote ECG monitoring and data storage system 100 with on-board data storage unit 120, a limited amount of ECG data 124 obtained can be stored in an on-board data storage unit 120. Because remote ECG monitoring and data storage system 100 is designed to be compact, physical space available for on-board data storage unit 120 is limited. The storage capacity of on-board data storage unit 120 is accordingly limited. In some embodiments, ECG data 124 is compressed by onboard digital processing carried out by data processing unit 122 prior to being stored in on-board data storage unit 120, to minimize the amount of memory required to store ECG data 124.

In one example embodiment, on-board data storage unit 120 is an internal memory unit that is capable of storing ECG data 124. On-board data storage unit 120 allows remote ECG monitoring and data storage system 100 to be used independently of receiving device 200 to collect and store ECG data 124. The ability to use remote ECG monitoring and data storage system 100 without simultaneously using a receiving device 200 can be important, for example, in situations in which a user experiences an abnormal physical sensation or abnormal heart pattern, and wishes to record ECG data from such abnormal experience for later review and analysis by a physician and does not have a receiving device 200 available, or does not have time to pair remote ECG monitoring and data storage system 100 and receiving device 200. In some embodiments, on-board data storage unit 120 is the on-chip memory of on-board processing unit 122, which minimizes the size of on-board data storage unit 120. In some embodiments, on-board data storage unit 120 is a separate memory unit embedded within system 100. In some embodiments, on-board data storage unit 120 is capable of storing at least 2 minutes, at least 5 minutes, at least 10 minutes, at least 15 minutes, or at least 20 minutes of ECG data 124.

If the ECG data is collected independently of a receiving device (i.e. when system 100 is not paired with a receiving device), at a later time, on-board processing unit 122 can be used to read stored ECG data 124 from on-board data storage unit 120 and pass the ECG data 124 to wireless transceiver 130 for transmission to receiving device 200. In alternative embodiments, on-board processing unit 122 can pass ECG data 124 directly to wireless transceiver 130 to be passed to receiving device 200 simultaneously while the ECG data is collected if the remote ECG monitoring and data storage system 100 is in communication with receiving device 200 (i.e. when system 100 is paired with receiving device 200).

Any suitable wireless communication device can be used to provide wireless transceiver 130. The type of communication device used to provide wireless transceiver 130 should be compatible with the wireless communication methods provided for by receiving device 200, so that wireless transceiver 130 can communicate with receiving device 200. For example, in some embodiments, wireless transceiver 130 communicates using a Bluetooth Low Energy (BLE) wireless communications link. In alternative embodiments, any suitable wireless communication protocol is used, e.g. WiFi, ZigBee, and ANT.

In some embodiments, wireless transceiver 130 uses an encrypted communication protocol to help maintain the confidentiality of the transmitted ECG data 124. Any suitable encrypted communications protocol now known or subsequently developed can be used in alternative embodiments.

In some embodiments, given the limited space available in on-board data storage unit 120, a data compression scheme is implemented by an algorithm provided on on-board data processing unit 122 to compress the ECG data 124 that is provided to on-board data storage unit 120. Any suitable data compression scheme now known or subsequently developed can be used in alternative embodiments. For example, on-board data processing unit 122 can use a delta modulation technique to compress the ECG data 124. In some embodiments, when receiving device 200 is paired with system 100 and ECG data 124 is being transmitted directly to receiving device 200, a data compression scheme is not used by data processing unit 122. In some embodiments, even when receiving device 200 is paired with system 100 and ECG data 124 is being transmitted directly to receiving device 200, a data compression scheme is applied to the transmitted data by data processing unit 122.

In some embodiments, data processing unit 122 is a low-power microcontroller platform.

Any suitable device capable of reading, manipulating and displaying data can be used as receiving device 200, e.g. a smartphone, smartwatch or other wearable computer system, tablet, laptop, desktop computer, or the like.

Receiving device 200 is provided with a suitable application program that is capable of processing data received from remote ECG monitoring and data storage system 100 via a suitable communications protocol, visually displaying ECG data 124, for example as a waveform shown on a graphic display of the receiving device 200, and facilitating other uses of ECG data 124 as described below, as well as manipulating and controlling remote ECG monitoring and data storage system 100.

Figure 4:
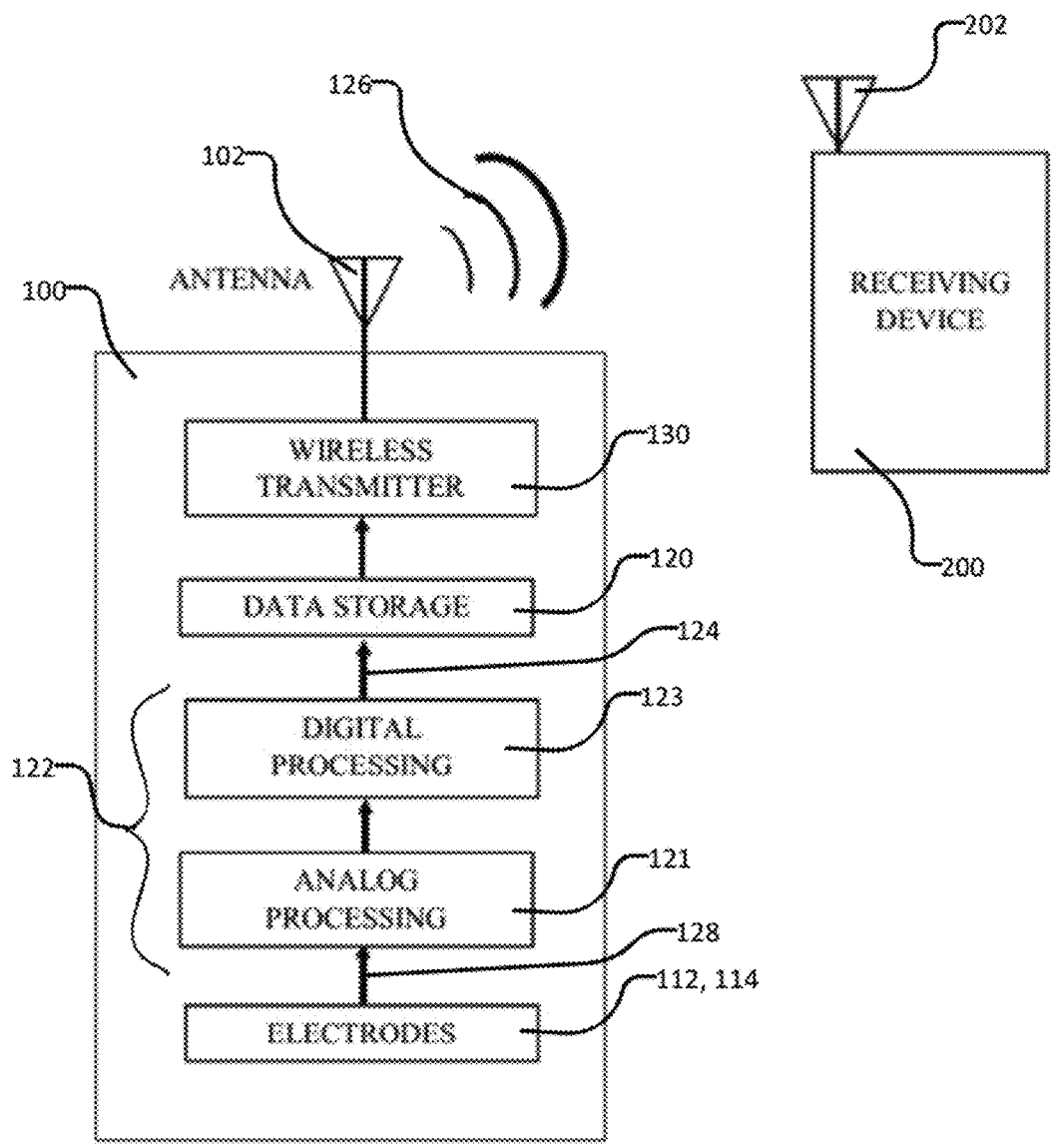
FIG. 4 shows an example embodiment of processing ECG signals detected by the system using both analog and digital processing.

With reference to FIG. 4, an example embodiment of a system 100 in which data processing unit 122 carries out both analog processing 121 and digital processing 123 of ECG signals 128 prior to providing ECG data 124 to on-board data storage unit 120 is illustrated. Either simultaneously with storage of ECG data 124 in on-board data storage unit 120 or at a later time, wireless transceiver 130 is used to transmit ECG data 124 to receiving device 200. In some embodiments, including the illustrated embodiment, both system 100 and receiving device 200 are provided with an appropriate antenna, illustrated schematically as antenna 102 and antenna 202, respectively, for allowing the exchange of wireless communications 126 between system 100 and receiving device 200.

In some embodiments, antenna 202 is embedded within housing 110. In some embodiments, antenna 202 projects outwardly from housing 110 (and is thus visible to a user).

In some embodiments, a power-saving mode is provided for system 100. When electrodes 112, 114 are in direct contact with the skin of a user, an extra-low power circuit is activated. When the extra-low power circuit detects a predefined tapping pattern of electrical contact applied by a user onto electrodes 112, 114, system 100 starts pairing with receiving device 200 via wireless transceiver 130 and transmitting wireless signals 126, including ECG data 124, to receiving device 200. Thus, remote ECG monitoring and data storage system 100 is using power to either or both (a) initiate pairing and (b) transmit wireless signals 126 only when the system 100 is paired with a receiving device 200.

In some embodiments, remote ECG monitoring and data storage system 100 is provided with an activation mechanism to initiate the obtention and recording of ECG data and/or the transmission of ECG data to receiving device 200. In some such embodiments, after a predetermined period of inactivity, system 100 enters a low power mode, in which ECG data is not recorded, processed or transmitted, and/or in which ECG data is not transmitted to receiving device 200. When the activation mechanism is activated, these functions, including pairing with receiving device 200 if present, are initiated.

Figure 5:
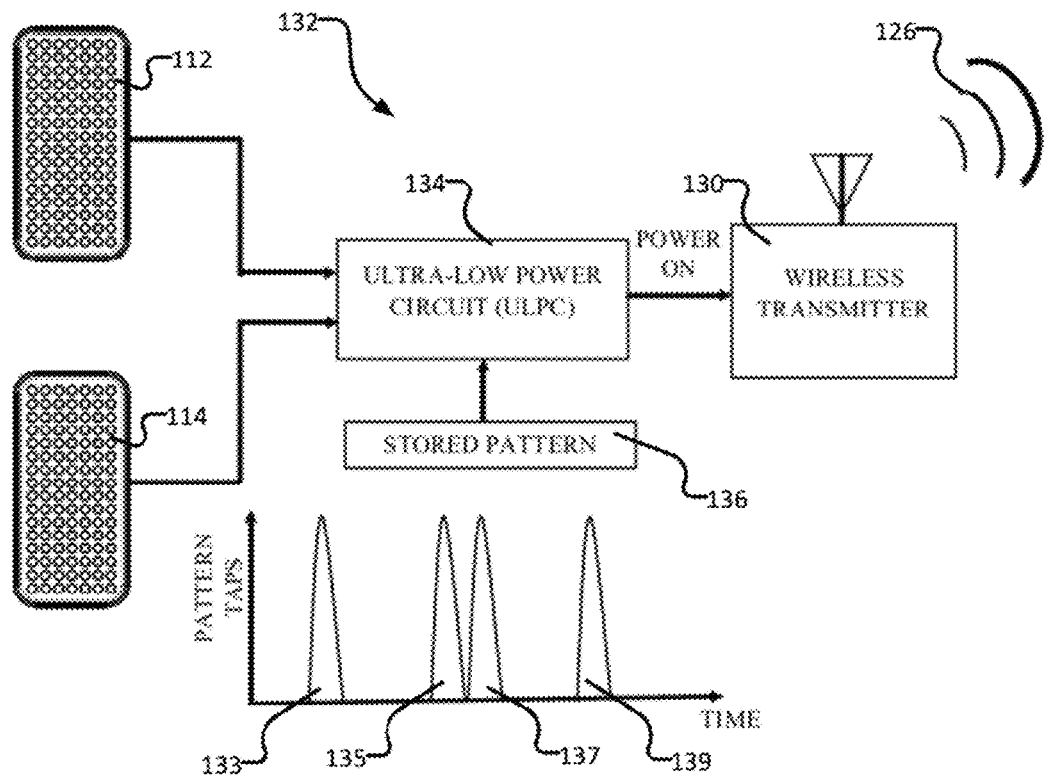
FIG. 5 shows schematically the operation of an example embodiment of a power saving mode provided in some embodiments.

In one example embodiment, as illustrated in FIG. 5, an ultra-low power circuit 134 is used as the activation mechanism 132 to pair receiving device 200 and system 100. The circuit 134 is activated when it detects the presence of an electrical voltage and current, e.g. as would occur when a user applies his or her fingers to electrodes 112, 114. Once the circuit 134 is activated, circuit 134 checks for the presence of a specific predetermined tapping pattern of electrical contact in the applied electrical voltages. If the specific predetermined tapping pattern of electrical contact 136 is detected, pairing is initiated and wireless transmission of ECG data 124 to receiving device 200 as wireless signals 126 is initiated by data processing unit 122. If the specific predetermined tapping pattern of electrical contact 136 is not detected, then system 100 remains in an inactive mode (i.e. not pairing and not transmitting any ECG data 124), thereby minimizing power consumption. The requirement for the presence of a specific predetermined tapping pattern of electrical contact 136 helps to ensure that system 100 is not erroneously activated by a passing touch of the fingers of a user over electrodes 112, 114, for example as might occur when a user moves or repositions system 100.

In the illustrated embodiment of FIG. 5, in one example embodiment, predetermined stored pattern of electrical contact 136 comprises a series of four taps, with a first tap of electrical contact 133 occurring at a first point in time, followed by a brief period of no contact (e.g. 0.5-2 seconds of time), followed by two successive taps of electrical contact 135, 137 with no time gap therebetween, followed by a further brief period of no contact (e.g. 0.5-2 seconds of time), followed by a final tap of electrical contact 139. The exact combination of taps and the length of periods of no tapping could be varied in alternate embodiments. The user must know the predetermined stored tapping pattern of electrical contact 136 in order to be able to activate the system, and the system must store the predetermined tapping pattern of electrical contact 136. In some embodiments, a programming mode is provided by an application program running on receiving device 200 to allow a user to enter or change predetermined stored tapping pattern of electrical contact 136. In some embodiments, the programming mode allows a user to apply a tapping pattern of electrical contact of the user's choosing; the application program records the tapping pattern of electrical contact applied by the user and stores this pattern as the predetermined tapping pattern of electrical contact 136.

In the embodiment of FIG. 5, ultra-low power circuit 134 is always active and monitors for electrical signals between electrodes 112, 114. In one embodiment, ultra-low power circuit 134 measures the electrical impedance between electrodes 112, 114 in order to monitor for electrical signals between electrodes 112, 114. In one embodiment, ultra-low power circuit detects the presence of an electrical voltage between electrodes 112, 114, which arises because a potential difference is crated between the electrodes when contacted by the user's fingers. In one embodiment, ultra-low power circuit 134 measures saturation of the preamplifier stage due to non-existence of operational amplifier bias currents. In this embodiment, in the absence of an electrical contact established through the fingers of a user, no DC bias current can be provided to high-impedance inputs of the preamplifiers; thus, either or both of the preamplifiers will be in saturation mode. This condition will be detected by the internal logic circuit of the ultra-low power circuit, resulting in power not being provided to wireless transceiver 130.

Regardless of how the electrical signals are detected, ultra-low power circuit 134 compares the pattern of taps of electrical contact applied by the user with stored pattern of electrical contact 136. If the pattern of taps applied by a user matches stored pattern of electrical contact 136, then power is provided to wireless transceiver 130 from power storage unit 140. Wireless transceiver 130 establishes wireless communication with receiving device 200 and transmits acquired ECG data 124 to receiving device 200 via wireless signals 126.

In some embodiments, the ratio between the power consumed by the ultra-low power circuit 134 to the power needed to operate wireless transceiver 130 is approximately 1:1000. Thus, the amount of power used by system 100 can be minimized in embodiments employing such an activation mechanism such as activation mechanism 132 to initiate transmission of stored ECG data 124 to receiving device 200.

In various embodiments, any suitable tapping pattern of electrical contact can be used for stored tapping pattern of electrical contact 136. In some embodiments, stored tapping pattern of electrical contact 136 is selected to be long enough that the wireless transceiver 130 is not activated by spurious or random contact of a user's fingers with electrodes 112, 114. In some embodiments, stored tapping pattern of electrical contact 136 is selected to be short enough that a user can easily remember the stored tapping pattern of electrical contact 136 and can execute stored tapping pattern of electrical contact 136 within a few seconds. In some embodiments, Barker codes are used as stored tapping patter of electrical contact 136.

In some embodiments, when activation mechanism 132 detects a specific pattern of taps of electrical contact applied by user, data processing unit 122 activates wireless transceiver 130 and begins pairing followed by wireless transmission of ECG data 124 from on board data storage unit 120 to receiving device 200, so that the ECG data 124 can be visualized, e.g. as a waveform, and further processed using the application program provided on receiving device 200.

In such embodiments, the energy usage of remote ECG monitoring and data storage system 100 is minimized, because system 100 is not continuously or regularly transmitting via wireless transceiver 130 in an effort to determine whether receiving device 200 is present and paired to receive data from system 100. Wireless transceiver 130 is active only when it has been specifically activated by a user.

In some embodiments, e.g. as illustrated in FIG. 3, a memory full signal 150, e.g. a warning light, vibration or audible tone, is activated via a suitable signal unit 152 provided on system 100, to inform a user when the on-board data storage unit 120 is full.

Figure 6:
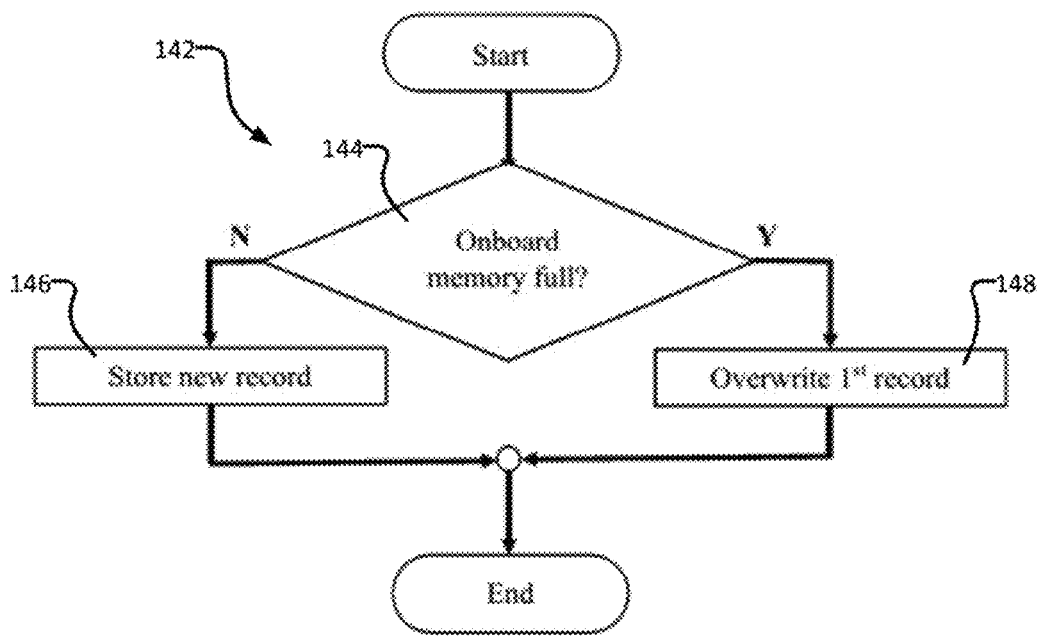
FIG. 6 shows an example embodiment of writing ECG data to a circular memory.

In one example embodiment, as shown in FIG. 6, data is managed in data storage unit 120 using a circular buffer (circular memory) 142. At step 144, data processing unit 122 determines whether on-board data storage unit 120 is full. If not, at step 146 data processing unit 122 stores a new record of ECG data 124 in on-board data storage unit 120. If on-board data storage unit 120 is full, at step 148, the oldest data record in on-board data storage unit 120 is overwritten.

In some embodiments, the memory in on-board data storage unit 120 is configured so that on-board data storage unit 120 will provide an indication that its memory is full, meaning that any new ECG data 124 that is recorded will overwrite previously recorded ECG data 124. On-board data storage unit 120 communicates the fact it is full to data processing unit 122, which in turn activates signal unit 152 to warn a user before previously recorded ECG data 124 is overwritten by generating a memory full signal 150. The user then has the opportunity to decide whether to proceed with a new recording which will replace the oldest one by overwriting previously stored ECG data 124 in on-board data storage unit 120, and can positively confirm this, e.g. by continuing to hold his or her fingers on electrodes 112, 114 to maintain electrical contact therewith for at least a predetermined period of time to indicate that the user does indeed wish to overwrite previously store ECG data 124, before data processing unit 122 will overwrite previously stored data in on-board data storage unit 120. The predetermined period of time can be any suitable period of time, for example at least 2, 3, 4, 5, 6, 7, 8, 9 or 10 seconds in some embodiments. In some embodiments, an application program running on receiving device 200 has a programming mode that allows a user to alter the predetermined period of electrical contact required to overwrite previously stored data in on-board data storage unit 120.

Any suitable indicator that is capable of producing a signal perceptible by a user can be used to provide signal unit 152, e.g. an indicator or warning light, including a change in color of an indicator light, e.g. from green to red, a unit capable of generating an audible signal, e.g. a tone or beep, a vibrator, or the like. Memory full signal 150 can accordingly be any signal that can be perceived by a user, whether audible, visible, or perceptible by feel.

In some embodiments, if a user determines that the previously recorded ECG data 124 should not be overwritten, the user must take further steps to create a copy of the previously recorded ECG data 124 prior to using remote ECG monitoring and data storage system 100 to record new ECG waveform data 124. For example, the user could cause system 100 to be paired with receiving device 200, so that the previously stored ECG data 124 can be downloaded into a suitable application program on receiving device 200 for further analysis and manipulation before new ECG data 124 is recorded in on-board data storage unit 120.

In some embodiments, once ECG data 124 has been transferred to receiving device 200, the memory in on-board data storage unit 120 is cleared, so that the user can record additional ECG data 124.

In some embodiments, the ECG data 124 are processed and transmitted wirelessly as wireless signals 126 from remote ECG monitoring and data storage system 100 through wireless transceiver 130 to receiving device 200. In some embodiments, when system 100 is paired with receiving device 200, all of the data contained in on-board data storage unit 120 is transferred to receiving device 200, so that the memory in on-board data storage unit 120 is cleared.

An application program running on a receiving device 200 can perform various functions, including displaying ECG data 124 in a visual format, e.g. as an ECG waveform. In some embodiments, receiving device 200 uses artificial intelligence and data driven models to detect and predict diseases based on the received ECG data 124. In some embodiments, a user can view, zoom, scroll, save and transmit the ECG data 124 and associated details (e.g. username, date and time that the ECG data 124 was obtained, any notes or comments added to the data file by the user, and so on) to a cloud-based server where the user can share such data with a physician. The physician may review data from one or more patients by accessing the server.

In some embodiments, data is encrypted prior to transmission to a cloud-based server, so that data integrity and confidentiality are protected. Any suitable data encryption scheme now known or later developed can be used in alternative embodiments.

With continued use, power storage unit 140 will gradually be depleted. A suitable mechanism for charging power storage unit 140 to allow for continued usage of remote ECG monitoring and data storage system 100 is provided. Any suitable recharging mechanism can be used.

In some embodiments, system 100 is recharged by a wireless charging system. The wireless charging system can be an inductive wireless charging system, a capacitive charging system, a solar cell, a sound/ultrasound wave charger, a movement charger or the like. For example, in some embodiments, system 100 is charged wirelessly by an inductive wireless charging station. In some such embodiments, system 100 is hermetically sealed and waterproof. The lack of any wired connection, e.g. a USB port, may allow charging and usage of system 100 even under wet conditions. Without being bound by theory, the inductive charging station is likely to require less space for integration within system 100 than might be the case for other recharging systems.

Figure 7:
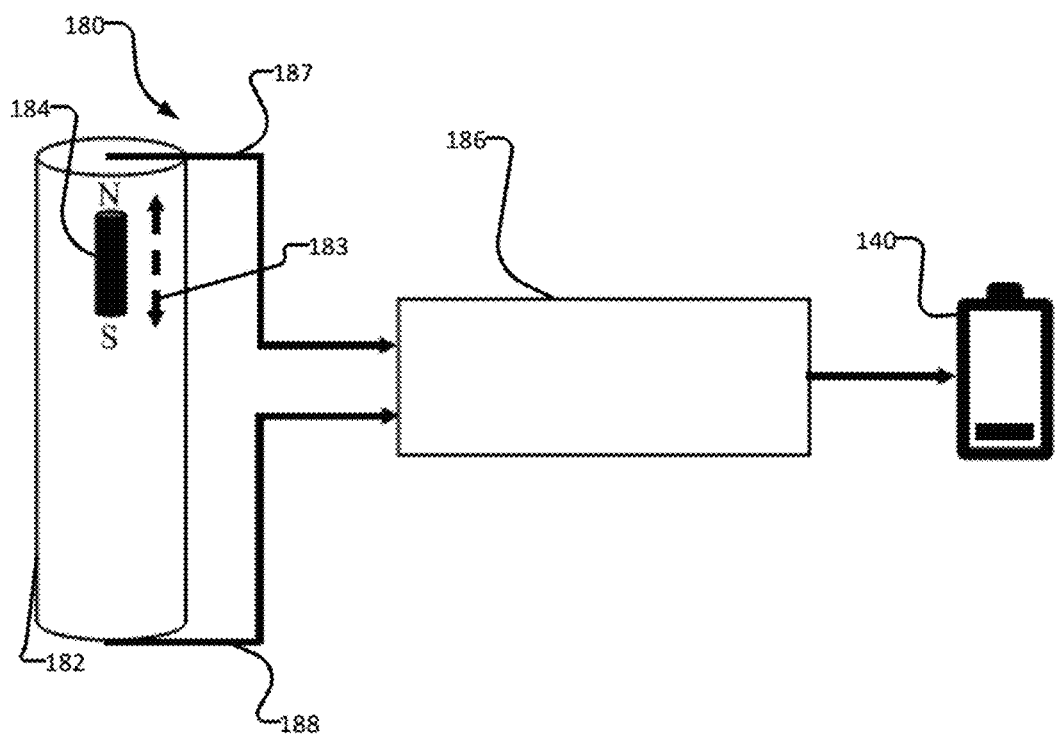
FIG. 7 shows an example embodiment of an electromechanical assembly for supplying power to recharge a power source.

In some embodiments, power storage unit 140 is recharged using power harvested from the mechanical movement of the wearer, for example as the user walks, exercises, or experiences acceleration caused by various modes of transport such as cars, airplanes, motorbikes, boats or the like. In one example embodiment, as illustrated in FIG. 7, a miniature electro-mechanical assembly for harvesting energy 180 is embedded within housing 110 of system 100. In one example embodiment, first and second power generating members, e.g. a coil of wire 182 and a magnet 184, are provided. The first and second power generating members are movable relative to one another, e.g. either one of coil of wire 182 or magnet 184 are free to move with respect to the other of magnet 184 or coil of wire 182, for example as illustrated by arrow 183, magnet 184 can move longitudinally with respect to coil of wire 182. Relative movement of magnet 184 and coil of wire 182 creates a change in the magnetic flux. By virtue of Faraday's law an electrical current will thereby be generated. This electrical current is collected by a pair of current collecting wires 187, 188 connected at the longitudinal ends of coil of wire 182 and passed to power rectifier circuit 186.

The electrical current so generated is electronically processed by a power rectifier circuit 186, so that it is suitable to feed to power storage unit 140. Thus, power storage unit 140 can be recharged by the mechanical movements of a wearer.

The relative movements of the first and second power generating members can be due to various sources of movement on the part of a user of system 100, as long as these sources of movement involve acceleration. For example, walking, jogging and accelerated motion during transport via any means (e.g. road, sea, or air) would create the required acceleration to cause relative movement of the first and second power generating members. The current by the relative movement, e.g. of magnet 174 and coil of wire 172, can be used to recharge power storage unit 140. In some such embodiments, sufficient energy can be harvested from the movement of a user that there is no need to connect system 100 to an external charger, and/or so that system 100 can continue to be used even when an external charging source is not available to recharge power storage unit 140.

In alternative embodiments, power storage unit 140 can be recharged using a microelectromechanical system (MEMS) using a piezoelectric material. The piezoelectric material can transform mechanical strain energy, e.g. caused by vibrations, to electrical energy that can be used to recharge power storage unit 140.

In some embodiments, electrodes 112, 114 are used to carry out the capacitive wireless charging. As any type of electrical conductor can be used to carry out capacitive wireless charging, the electrodes can themselves be used to carry out capacitive wireless charging. In this regard, while silver-silver chloride electrodes are a poor conductor of direct electric current, such electrodes can be used as plates for a capacitive charging system because the silver itself is a good conductor of electricity and can act as the capacitor plate for carrying out capacitive wireless charging, while the silver-silver chloride layer acts as the dielectric of the capacitor. In some embodiments, power storage unit 140 is an ultracapacitor or a supercapacitor.

Over time, with exposure to human skin and/or the atmosphere, in embodiments in which electrodes 112, 114 are made from brittle materials such as silver-silver chloride, electrodes can degrade, resulting in decreased signal integrity and therefore decreased quality of the ECG data obtained by the electrodes with the passage of time. In some embodiments, electrodes 112, 114 are replaceable, so that once the expected useful lifetime of electrodes 112, 114 has passed, such electrodes can be removed from housing 110 and replaced with new electrodes 112, 114. In some such embodiments, electrodes 112, 114 are disposable.

In some embodiments in which electrodes 112, 114 are made from silver-silver chloride, electrodes 112, 114 are recoatable with silver-silver chloride mixture 116 so that signal integrity can be maintained as the electrodes 112, 114 are used over extended periods of time. Recoatable electrodes can potentially reduce costs of replacing electrodes with new ones while preserving signal integrity, and/or can allow for regeneration of electrodes 112, 114 for further use in circumstances where replacement electrodes are not available. As described below, in some embodiments an apparatus is provided that can be used by a user to recoat electrodes 112, 114.

Figure 8:
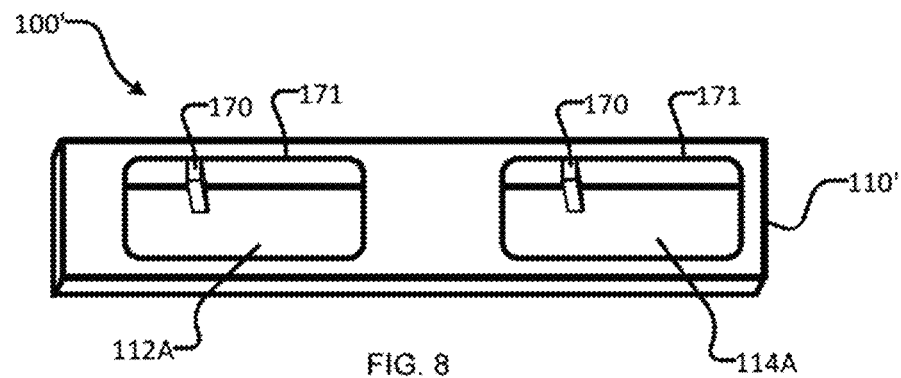
FIG. 8 shows a perspective view of a device for monitoring and/or recording ECG signals according to another embodiment, wherein the electrodes are removable.

In some embodiments, electrodes 112, 114 are detachable from housing 110, e.g. so that the electrodes can be replaced and/or recoated. For example, with reference to FIGS. 8 and 9, an example embodiment of a remote ECG monitoring and data storage system 100' having detachable electrodes is shown. System 100' is similar to system 100 and like elements are indicated by like reference numerals and are not further described again herein. System 100' differs from system 100 in that the electrodes are detachably mounted on housing 110'. After being removed from housing 110', the electrodes can be thrown away or recoated and reused.

Figure 9:
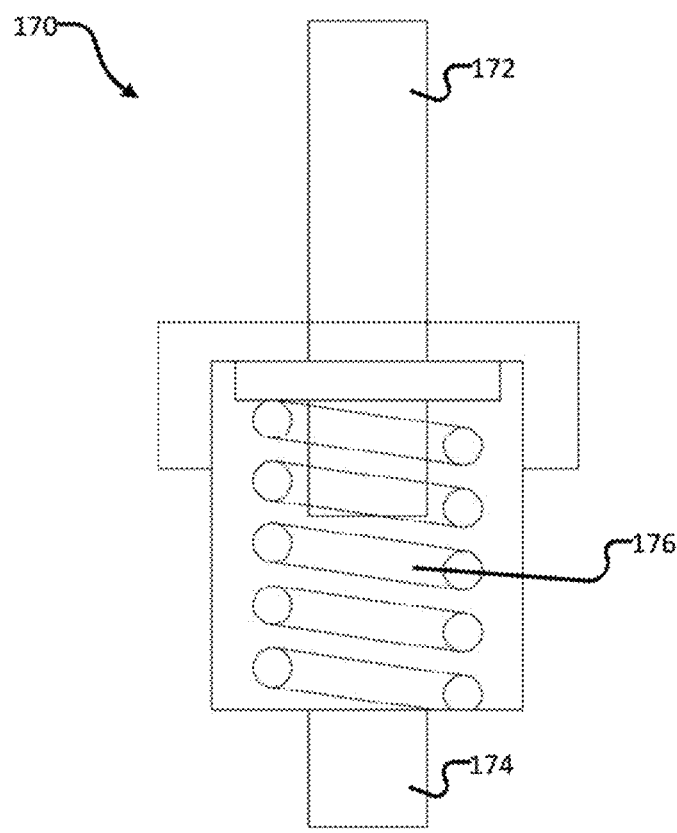
FIG. 9 shows an example embodiment of a pin-locking mechanism that can be used to secure detachable electrodes in position.

Any suitable mechanism for detachably securing the electrodes in place can be used in various embodiments of system 100'. In the illustrated example embodiment, a pin-locking mechanism 170, shown in more detail in FIG. 9, is used to detachably engage the electrodes with system 110'. A pair of receiving apertures 112A, 114A are provided in housing 110' to receive detachable electrodes 112, 114. To secure the electrodes in place using pin-locking mechanism 170, a user compresses the upper pin 172 of one of the pin-locking mechanisms 170 on housing 110'. A user then inserts the corresponding electrode, e.g. electrode 112, into the corresponding aperture 112A in housing 110' from the inner side of aperture 112A and seats that electrode 112 in position so that the upper pin 172 is seated within a corresponding securing aperture provided on the rear surface of the electrode 112 and the upper surface of electrode 112 is retained within housing 110' by press-fit engagement against a lip 171 formed in housing 110'.

The thickness of electrode 112 is such that when electrode 112 is secured in place interposing upper pin 172 and lip 171, upper pin makes does not make direct contact with lower pin 174. A resilient member such as coil spring 176 is engaged between both upper pin 172 and lower pin 174, and provides an outward force against upper pin 172 to hold electrode 112 sandwiched in place between upper pin 172 and lip 171. In this embodiment, when a user desires to use electrodes 112, 114 to obtain ECG data, the user must press slightly inwardly on both of electrodes 112, 114, to bring upper pins 172 into contact with lower pins 174 and thereby establish an electrical circuit between electrodes 112, 114.

A user can install electrode 114 within receiving aperture 114A in the same manner as described above for electrode 112. When a user wishes to remove electrodes 112, 114, a reverse process can be followed. For example, a user can push inwardly on electrode 112 to compress coil spring 176, to allow upper pin 172 and lower pin 174 to come into contact, so that electrode 112 will be provided with freedom of movement to allow upper pin 172 to be removed from the securing aperture provided on the rear surface of electrode 112. Electrode 112 can then be removed from receiving aperture 112A in an inward direction. A similar process can be followed to remove electrode 114 from receiving aperture 114A.

Other mechanisms such as a snap-on engagement, a friction fit, interlocking components that can be engaged in a suitable manner, e.g. via threaded or rotationally engageable components, a magnetic mechanism, or the like can be used to removably couple electrodes 112, 114 to housing 110' in alternative embodiments.

In some embodiments having removable electrodes 112, 114, remote ECG monitoring and data storage system 100' is provided as a kit having one pair of electrodes 112, 114 installed therein and an additional pair of uninstalled electrodes 112, 114 supplied therewith. When the first pair of electrodes 112, 114 requires recoating, a user can remove the first pair of electrodes 112, 114 and install the second pair of electrodes 112, 114 on housing 110. In this way, the user can continue using remote ECG monitoring and data storage system 100', even while the first pair of electrodes 112, 114 is being recoated.

In some embodiments, electrodes 112, 114 are permanently mounted to housing 110. In some such embodiments, electrodes 112, 114 are designed so that they can be recoated in situ, i.e. while mounted to housing 110. In such embodiments, a user does not need to remove electrodes 112, 114 to recoat them. In some embodiments, the fact that the electrodes 112, 114 are not detachable results in increased overall mechanical reliability of remote ECG monitoring and data storage system 100, as the electrodes do not need to be disconnected during the recoating process.

In some embodiments, the application program provided on receiving device 200 calculates the anticipated expected lifetime of electrodes 112, 114, for example by evaluating a number of different factors such as the age of electrodes 112, 114 and the number of cycles of ECG data obtained by electrodes 112, 114. As the anticipated useful lifespan of electrodes 112, 114 approaches, a user is given a warning signal by the application program to warn the user that electrodes 112, 114 should be replaced or recoated soon. In some embodiments, after the anticipated useful lifespan of electrodes 112, 114 has passed, the application program on receiving device 200 may generate an error message warning the user to immediately replace or recoat electrodes 112, 114 prior to recording new ECG data with system 100.

In some embodiments, remote ECG monitoring and data storage system 100 is configured to evaluate the quality of ECG signals produced by electrodes 112, 114. When the quality of ECG signals produced by electrodes 112, 114 falls below a predetermined threshold, either or both of remote ECG monitoring and data storage system 100 and receiving device 200 can be configured to provide a warning indication to a user to indicate that electrodes 112, 114 should be replaced or recoated soon.

In some embodiments in which electrodes 112, 114 are silver-silver chloride electrodes, a coating system is separately provided and used by a user to recoat electrodes 112, 114 with a silver-silver chloride layer. In some embodiments, the coating system applies a silver-silver chloride liquid or paste mixture onto electrodes 112, 114. This can be done by dipping, painting, spray coating, or the like. In one example embodiment, a coating system uses an electrolytic process to deposit a layer of silver-silver chloride onto electrodes 112, 114. In some embodiments, a layer of silver-silver chloride is created or regenerated by brushing a silver substrate with solution containing chloride ions.

In some embodiments, to recoat removable electrodes, a user removes electrodes 112, 114 from system 100 and cleans them using a mild hydrogen chloride (HCl) solution. Once cleaned, the electrodes are placed in a coating apparatus that electrolytically deposits a layer of silver chloride onto the silver core of the electrodes by passing an electric current through the electrodes. In some example embodiments, the electrolytic process uses sodium chloride (NaCl) or potassium chloride (KCl) as common salts. In some embodiments, the electrolytic process is time-controlled, and is repeated until a uniform light gray colour appears on the electrode.

In some embodiments, to recoat non-removable electrodes, recoating is carried out in situ (i.e. while the electrodes 112, 114 remain in system 100). A protective disposable plastic cover is placed over housing 110, or the regions of housing 110 proximate electrodes 112, 114. Electrodes 112, 114 remain exposed, and a layer of silver chloride is created by applying a solution containing chloride ions to the silver core of electrodes. In one example embodiment, a brush soaked in sodium hypochlorite (NaOCl), sold commercially as bleach, is used to deposit chloride ions (Cl$^-$) onto the silver core of electrodes. In some embodiments, the coating process is repeated until a light gray colour is obtained on the surface of electrodes 112, 114.

In some embodiments, the recoating apparatus is dimensioned to accommodate various different sizes of electrodes, e.g. as might be used on different sized or shaped embodiments of remote ECG monitoring and data storage system 100. In some embodiments, the recoating apparatus is dimensioned to accommodate various different sizes and shapes of remote ECG monitoring and data storage system 100, for example in embodiments in which electrodes 112, 114 are recoated in situ without being removed from housing 110.

Figure 10:
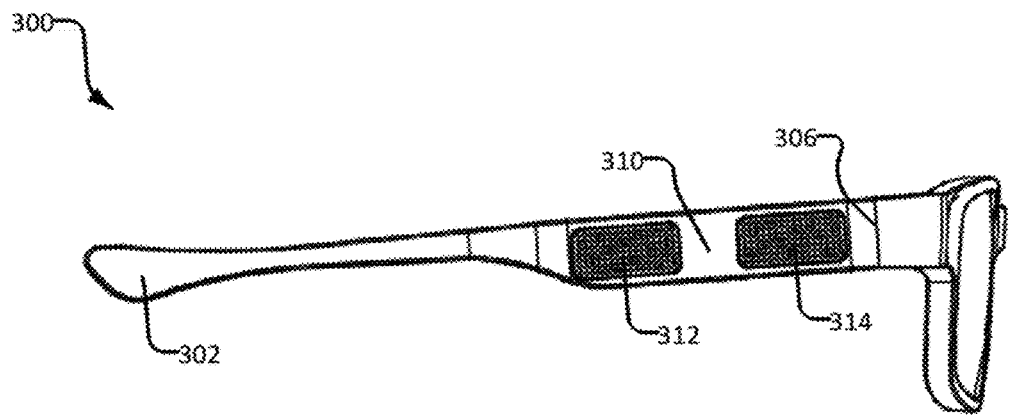
FIG. 10 shows a side elevation view of a pair of eyeglasses for monitoring and/or recording electrocardiographic signals according to one embodiment of the present disclosure.
Figure 11:
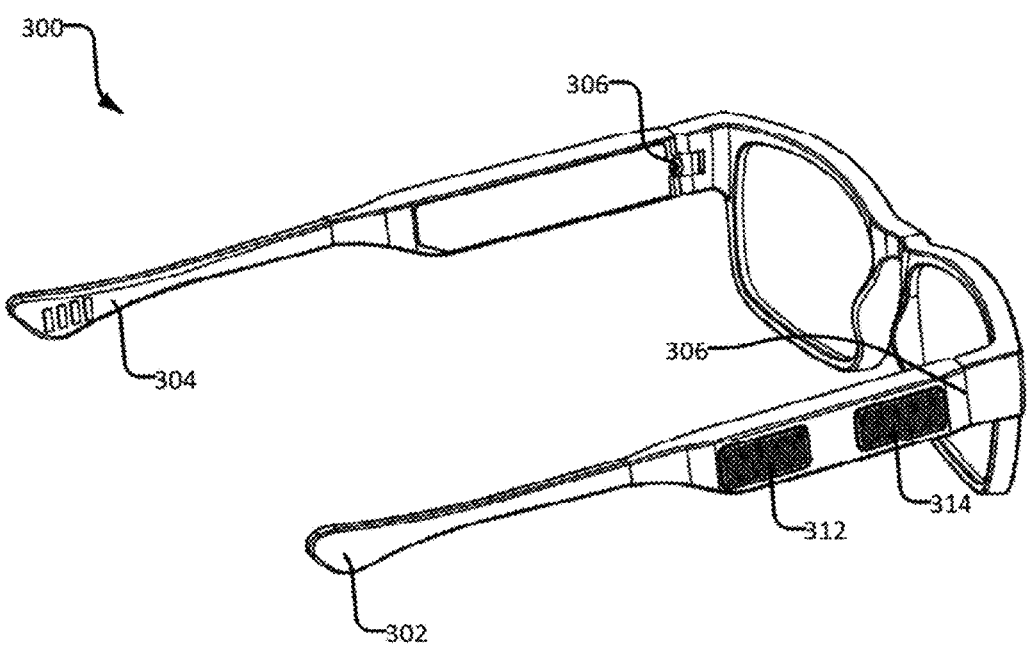
FIG. 11 shows a perspective view of the embodiment of FIG. 10.

FIGS. 10 and 11 show an example embodiment in which a remote ECG monitoring and data storage system is embodied in a pair of eyeglasses 300 for monitoring and/or recording ECG signals. Components of eyeglasses 300 that correspond with components of remote ECG monitoring and data storage system 100 described above are illustrated with reference numerals incremented by 200, and their function is not described again herein for the sake of brevity.

In the illustrated embodiment, electrodes 312, 314 are embedded in the same side handle (or arm) 302, on the right side, of the frame of eyeglasses 300. In alternative embodiments, electrodes 312, 314 are both embedded in the left arm 304 of eyeglasses 300. Without being bound by theory, having both electrodes 312, 314 on the same arm (i.e. on the same side of the glasses) may simplify electronic integration of the components of the remote ECG monitoring and data storage system within the frame of glasses 300. This is because wires do not need to run throughout the frame, and in particular wires do not need to extend through hinges 306 of the frame of eyeglasses 300. As such, manufacturing may be less complex than embodiments in which the electrodes are embedded in different arms of the glasses frame, for which wires need to extend through hinges 306. For some embodiments, this may decrease production costs and increase the overall reliability of the system.

To use eyeglasses 300 to monitor or record ECG signals, a user can remove eyeglasses 300 and use one finger from each hand to hold a respective one of the arms 302, 304 of eyeglasses 300 to establish electrical contact with electrodes 312, 314. Alternatively, the user can leave eyeglasses 300 in place on the user's head, and extend each arm upwardly to allow one of the user's fingers from each hand to make contact with electrodes 312, 314 while the user is wearing eyeglasses 300 in a conventional manner.

In alternative embodiments, electrodes 312, 314 are embedded in different arms of the glasses frame, e.g. first electrode 312 is provided in left arm 304 of eyeglasses 300, and second electrode 314 is provided in right arm 302 of eyeglasses 300. Without being bound by theory, such embodiments may provide greater convenience for some users, because a user will be able to establish contact between his or her fingers and the electrodes by extending his or her arms upwardly to the corresponding same side of the eyeglasses 300, e.g. the left hand fingers of the user will make contact with the electrode on the left arm of the glasses frame, and the right hand fingers of the user will make contact with the electrode on the right arm of the glasses frame. In alternative embodiments, users could alternatively choose to extend their respective fingers to the opposite side arm of the glasses frame (e.g. the right hand fingers of the user could contact the electrode on the left arm of the glasses frame, and the left hand fingers of the user could contact the electrode on the right arm of the glasses frame).

In some embodiments in which electrodes 312, 314 are embedded in different arms of the glasses frame, eyeglasses 300 are provided with a neck strap coupled to the right and left arms 302, 304 of the glasses frame. In such embodiments, the wires used to connect electrodes 312 and 314 with the other components of system 300 extend through the neck strap, which avoids a need to run wires through hinges 306 of eyeglasses 300.

In some embodiments, electrodes 312, 314 are pivotably mounted to eyeglasses 300, so that electrodes 312, 314 can be rotated outwardly away from housing 310 of eyeglasses 300. In some such embodiments, the ease of use of electrodes 312, 314 by a user may be enhanced, e.g. because a user can readily pinch each one of electrodes 312, 314 between his or her index fingers and thumbs, which may make it easier for a user to maintain a steady contact with electrodes 312, 314 than if a user is simply pressing his or her fingers against electrodes 312, 314 that are mounted flush with housing 310.

Electrodes 312, 314 can be compatible with a variety of glasses frames, to allow a user to select a style of eyeglasses 300 that is desirable to the user.

Figure 12:
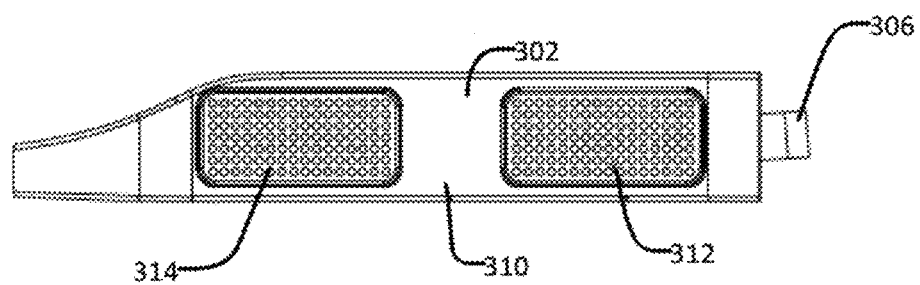
FIG. 12 shows a partial view of the right arm of an example embodiment.
Figure 13:
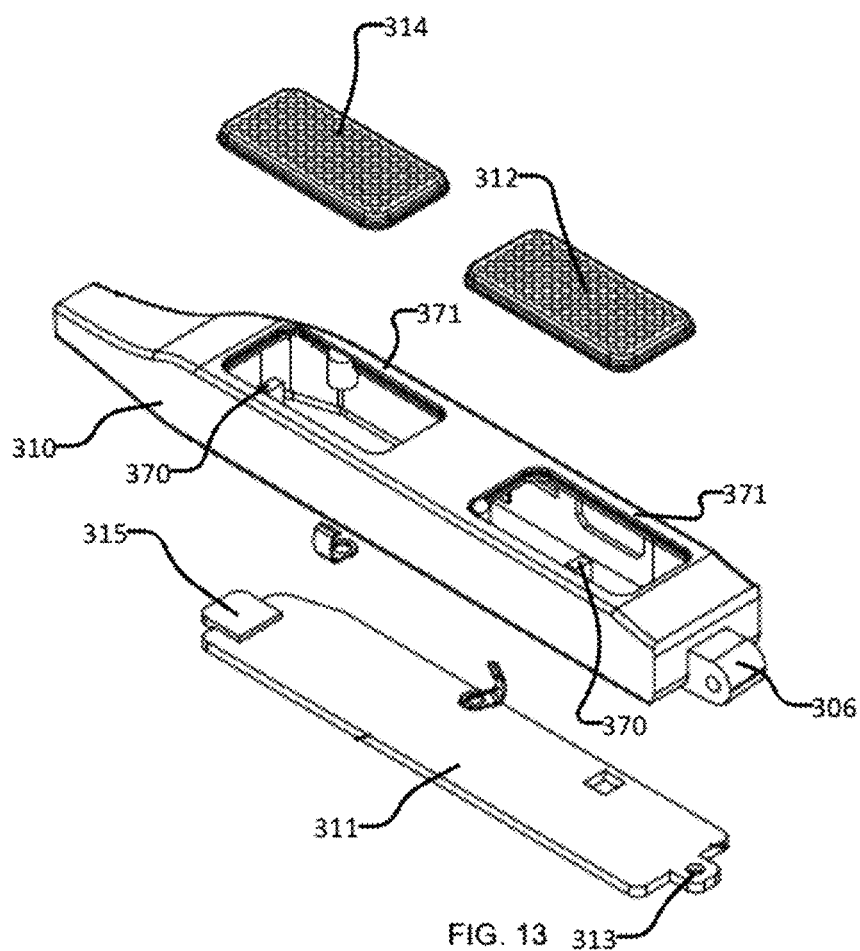
FIG. 13 shows an exploded view of the right arm of an example embodiment in which the electrodes are detachable.

FIGS. 12 and 13 show an example embodiment of a right arm 302 of eyeglasses 300 where right arm 302 is configured to engage with removable electrodes 312, 314. In the illustrated embodiment, electrodes 312, 314 are detachably engaged with the housing 310 via a pin-locking mechanism 370 that is similar in structure and function to pin-locking mechanism 170.

In the illustrated embodiment of FIGS. 12 and 13, all of the components of remote ECG monitoring and data storage system 300 corresponding to components of system 100 (e.g. on-board data storage unit, data processing unit, power storage unit, signal unit, wireless transceiver, and so on) are positioned within the space defined between housing 310 and a backing plate 311 that is detachably engageable with housing 310. In the illustrated embodiment, backing plate 311 includes an aperture 313 at a first end thereof for receiving a fixing screw or latch that is secured in threaded engagement with a corresponding receptacle on housing 310 and a snap-fit member 315 at a second end thereof for engaging in a snap-fit with a corresponding snap-fit receiving member provided on housing 310.

In the illustrated embodiment of FIGS. 12 and 13, to remove electrodes 312, 314, a user removes backing plate 311 from housing 310. For example, the fixing screw is removed from aperture 313 and snap-fit member 315 is disengaged from housing 310 to release backing plate 311. A user then compresses one of the pin-locking mechanisms 370 to allow a respective one of electrodes, e.g. electrode 312, to be removed from engagement with the pin-locking mechanism 370 and released out the rear of housing 310. A user then compresses the other one of the pin-locking mechanisms 370 to allow the other one of the electrodes, e.g. electrode 312, to be removed from engagement with the pin-locking mechanism 370 and released out the rear of housing 310.

With electrodes 312, 314 removed, a user can then recoat electrodes 312, 314 or opt to dispose of electrodes 312, 314. After electrodes 312, 314 have been recoated, or using a new replacement pair of electrodes 312, 314 if a user is disposing of the old electrodes or installing a new pair of electrodes 312, 314 while the old electrodes are being recoated, a user can install each of electrodes 312, 314 by compressing one of the pin-locking mechanisms 370, engaging a securing aperture on the rear surface of the corresponding electrode 312 or 314 with the upper pin 372 of the pin-locking mechanism 370, and allowing the resilient member such as coil spring 376 to push forwardly on upper pin 172 and thus electrode 312 or 314 to secure the electrode in place against a lip 371 of housing 310.

In alternative embodiments in which electrodes 312, 314 are not detachable, backing plate 311 can be permanently secured to housing 310, for example by application of suitable adhesives or ultrasonic welding techniques after eyeglasses 300 have been assembled for manufacture.

In some embodiments, electrodes 312, 314 are recoated without being removed from the frame of the glasses. Such electrodes are described as "in-situ" recoatable electrodes. In such embodiments, a fastening system for detachably securing electrodes 312, 314 does not need to be provided. Without being bound by theory, the use of in-situ recoatable electrodes can reduce recurring costs of replacing electrodes with new ones while preserving signal integrity. Additionally, the fact that the electrodes do not need to be detached during the coating process may increase the overall reliability of the glasses frame, and place less mechanical stress on the frame handle as well as components of the pin locking system, including in particular electrical connector 328.

In some embodiments, electrodes 312, 314 are removed from the frame of the glasses and then recoated, i.e. electrodes 312, 314 are detachable recoatable electrodes. Without being bound by theory, detachable recoatable electrodes may reduce recurring costs of replacing electrodes while preserving signal integrity. In this embodiment, to recoat electrodes 312, 314, both electrodes 312, 314 are removed from the glasses frame and placed in a silver-silver chloride coating apparatus. While electrodes 312, 314 are removed from the glasses frame, a user can continue using the glasses as desired, without the functionality provided by electrodes 312, 314. A user may optionally have two or more pairs of electrodes 312, 314, so that when one pair is being recoated, the user can use a different pair to ensure that ECG signals are being monitored and may be recorded at any desired time.

In some embodiments in which electrodes 312, 314 are not detachable, eyeglasses 300 are hermetically sealed and hence waterproof. The lack of any wired connection, e.g. a USB port, or detachment points for detachable electrodes may allow charging and usage of eyeglasses 300 even under wet conditions.

Figure 14:
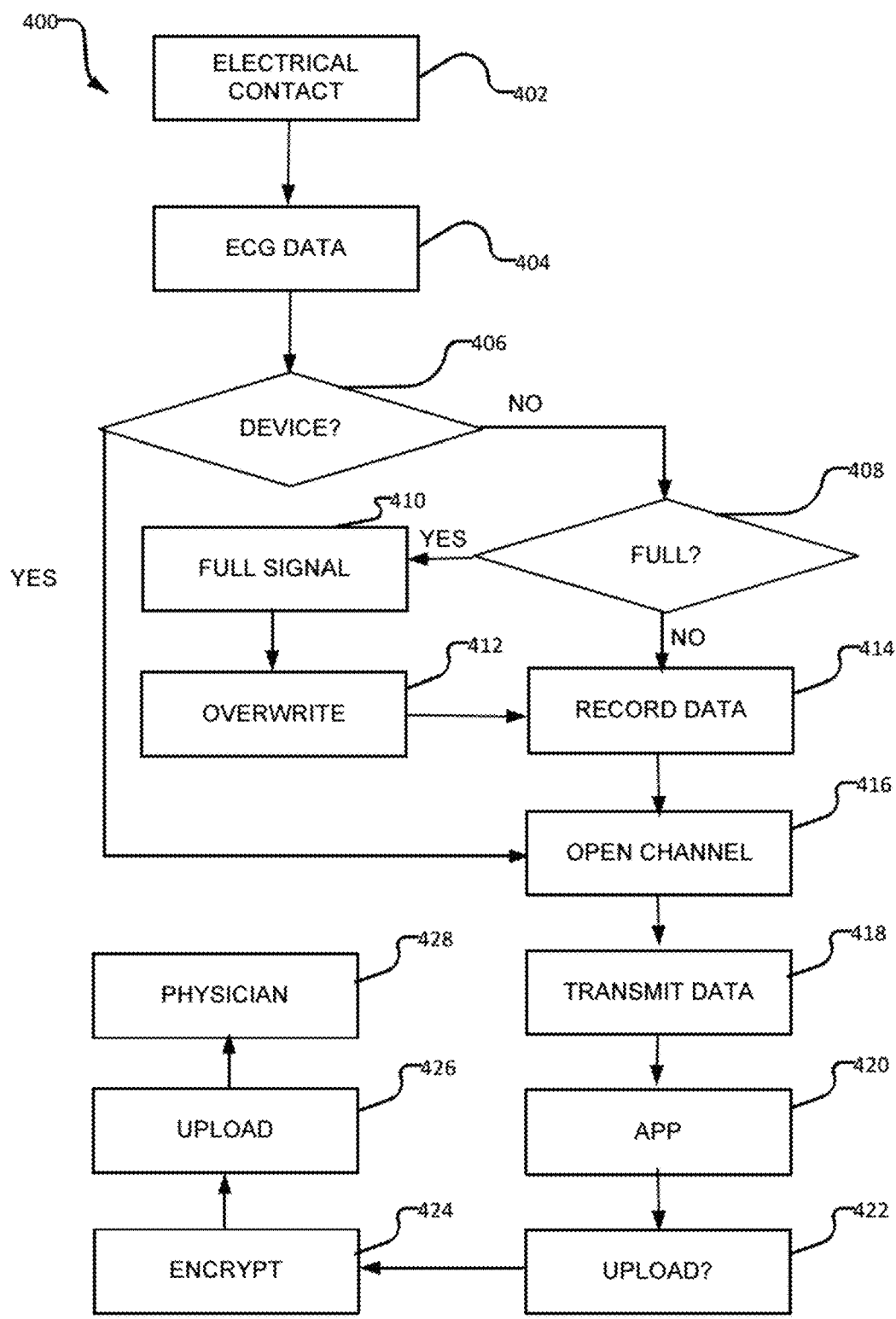
FIG. 14 shows a flow diagram of an example embodiment of a method for monitoring and/or and recording ECG signals.

FIG. 14 shows an example embodiment of a method 400 for monitoring and/or recording ECG signals. While for clarity the method 400 is described with reference to the structure of remote ECG monitoring and data storage system 100, any device capable of performing the recited functions could be used, e.g. remote ECG monitoring and data storage system 300.

To start detecting and monitoring ECG signals, a user establishes a stable electrical contact with the device via electrodes 112, 114. For example, at step 402, a user contacts his or her right- and left-hand finger tips to a respective one of the electrodes 112, 114, so that an electric current can pass from the first electrode 112 through a first finger of the user (e.g. a left finger), through the user's heart, and through the user's second finger (e.g. a right finger) to the second electrode 114, thereby providing an ECG signal.

In embodiments in which electrodes 112, 114 are detachable and are secured in place using pin-locking mechanism 170, a user applies sufficient force to electrodes 112, 114 to compress coil spring 176 to allow upper pin 172 to make electrical contact with lower pin 174 to establish a stable electrical contact.

At step 404, electrodes 112, 114 are activated and used to obtain ECG data 124 from the user. At step 406, data processing unit 122 determines that remote ECG monitoring and data storage system 100 is not paired with receiving device 200. At step 408, data processing unit 122 determines whether the circular memory in on-board data storage unit 120 is full, i.e. whether previously recorded ECG data 124 will be overwritten if new ECG data 124 is recorded. At step 410, if data processing unit 122 has determined that the circular memory in on-board data storage unit 120 is full, a memory full signal 150 is generated for the user, e.g. by illuminating or changing the colour of a warning light, by generating an audible signal or tone, or by generating a tactile sensation such as a vibration.

At step 412, the user has the option to indicate that the previously recorded ECG waveform data 124 in on-board data storage unit 120 should be overwritten, for example by continuing to maintain contact with electrodes 112, 114 for at least a predetermined period of time. The method then continues to step 414.

If at step 408, data processing unit 122 determines that the circular memory in on-board data storage unit 120 is not full, the method continues to step 414. At step 414, data processing unit 122 records up to ten minutes of ECG data 124 in on-board storage unit 120.

Subsequently, at step 416, a wireless communication channel is opened between remote ECG monitoring and data storage system 100 and receiving device 200. For example, in one embodiment, a user can apply a predetermined series of taps to system 100 to activate wireless transceiver 130. At step 418, wireless transceiver 130 transmits stored ECG data 124, together with any additional data recorded, such as the date and time that the ECG data 124 was obtained, to receiving device 200.

As an alternative, if at step 406, data processing unit 122 determines that remote ECG monitoring and data storage system 100 is paired with a receiving device 200, steps 408 to 414 can be omitted, and the method can proceed directly to step 416, by transmitting ECG waveform data 124 directly to receiving device 200 via wireless transceiver 130 in real time as ECG waveform data 124 is obtained.

At step 420, the transmitted ECG waveform data 124 is received in an application program running on receiving device 200. A user has the option to use the application program to manipulate and view the ECG data 124, e.g. viewing as an ECG waveform, scrolling, zooming, printing or the like, and by adding notes and comments to the data file (e.g. noting the location where the data was obtained, what activity the user was engaged in at the time the data was obtained, any unusual physical sensations or symptoms that the user was experiencing while the data was being recorded or that caused the user to feel the need to acquire the ECG data).

At step 422, the user has the option to use the application program to upload the ECG data 124 and any accompanying data to a secure cloud-based server for storage and for possible review by the user's physician. In some embodiments, receiving device 200 could send the ECG data 124 and any accompanying data as an SMS message or email message. At step 424, data is securely encrypted before being uploaded to the cloud-based server at step 426. At step 428, the user's physician can access and review the user's ECG waveform data 124.

Figure 15:
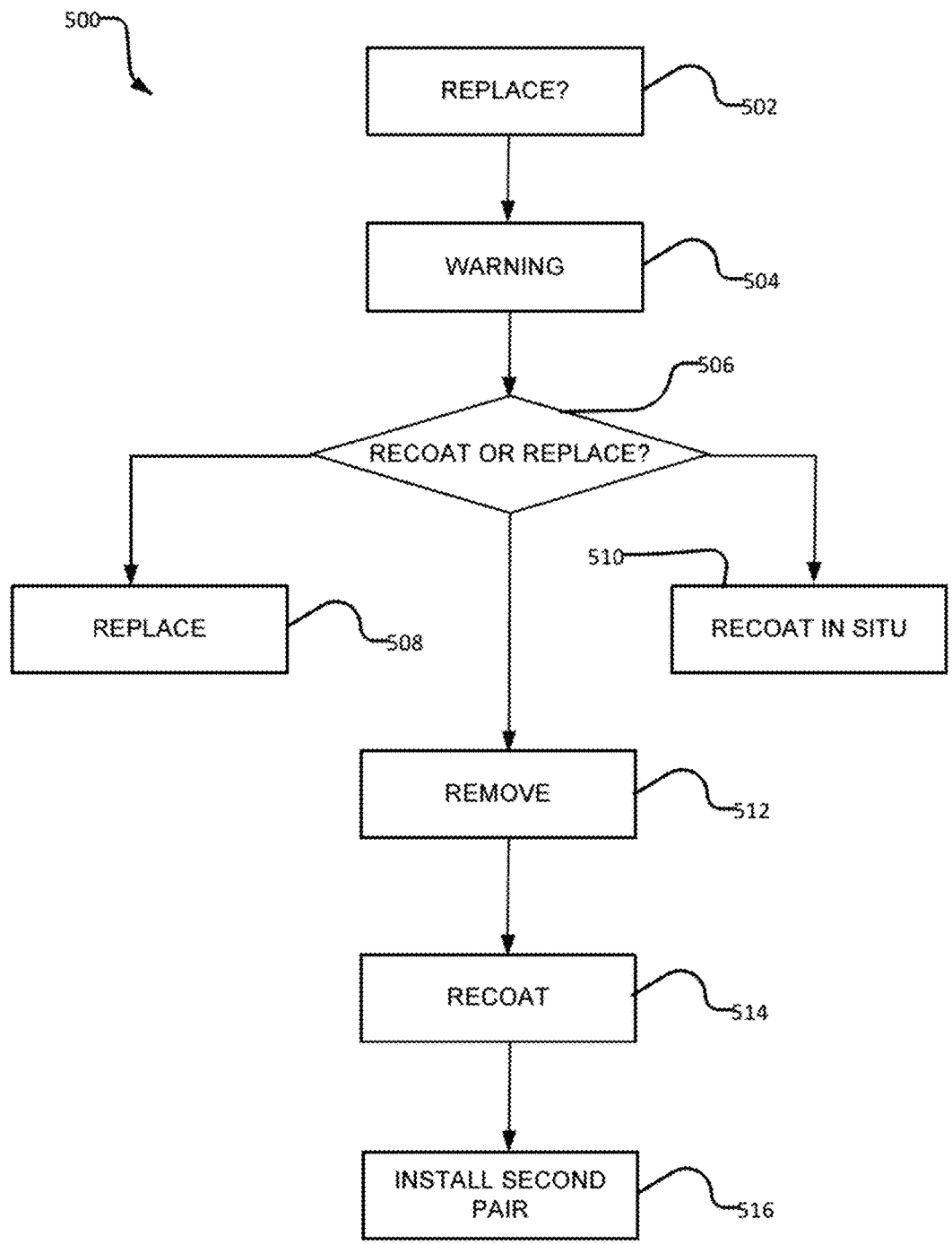
FIG. 15 shows a flow diagram of an example embodiment for recoating or replacing electrodes prior to the expiration of their expected useful lifetime.

With reference to FIG. 15, an example embodiment of a method 500 of using removable or recoatable electrodes 112, 114 is illustrated. At step 502, the application program running on receiving device 200 makes a determination based on the age and number of cycles of use of electrodes 112, 114 that electrodes 112, 114 are due to be replaced. Alternatively, at step 502, the application program running on receiving device 200 makes a determination of the quality of the ECG signal obtained by electrodes 112, 114 and if the quality falls below a predetermined threshold, the application program makes a determination that electrodes 112, 114 are due to be replaced. At step 504, the application program causes either receiving device 200 or remote ECG monitoring and data storage system 100 to provide a suitable warning message or indication, to war a user that electrodes 112, 114 are nearing the end of their expected reliable lifespan or are producing a lower than acceptable threshold ECG signal quality and should be replaced or recoated.

At step 506, a user takes appropriate action to replace or recoat electrodes 112, 114. For example, in embodiments in which electrodes 112, 114 are replaceable or disposable, at step 508, a user removes the old pair of electrodes 112, 114 and replaces them with a new pair of electrodes 112, 114.

In embodiments in which electrodes 112, 114 are recoatable in situ, a user provides remote ECG monitoring and data storage system 100 to a suitable recoating apparatus at step 510, so that electrodes 112, 114 can be recoated in situ, i.e. without being removed from remote ECG monitoring and data storage system 100.

In embodiments in which electrodes 112, 114 are removable and recoatable, at step 512, a user removes electrodes 112, 114 from remote ECG monitoring and data storage system 100 and supplies the electrodes 112, 114 to a suitable recoating apparatus at step 514 so that the electrodes 112, 114 can be recoated. In some embodiments in which system 100 is provided as part of a kit having at least two pairs of electrodes 112, 114, at step 516 a user installs the second pair of electrodes 112, 114 on system 100, so that the user can continue to record ECG signals even while the first pair of electrodes 112, 114 is being recoated.

Figure 16:
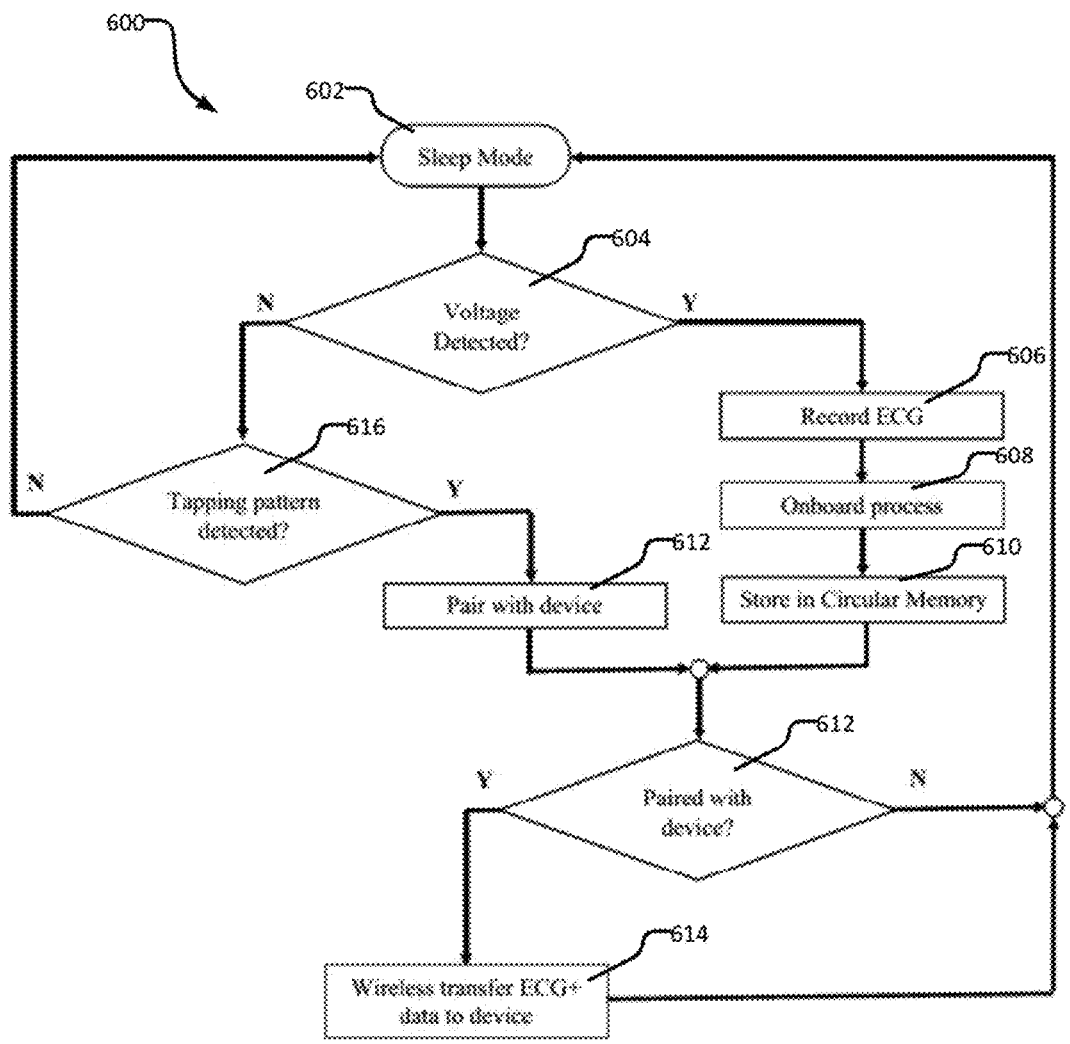
FIG. 16 shows a flow diagram of an example embodiment of a power-saving mode of operation.

With reference to FIG. 16, an example embodiment of a power-saving mode of operation 600 is illustrated with reference to the components of remote ECG monitoring and data storage system 100. It will be apparent to those skilled in the art that method 600 could be carried out using any suitable apparatus, and is not limited to a mode of operation of system 100.

At step 602, system 100 is in sleep mode. In sleep mode, wireless transceiver 130 is not actively operating, and therefore is not consuming power. While system 100 is in sleep mode, in the illustrated embodiment, a user can still use system 100 to obtain and record ECG data 124 by applying his or her fingers to electrodes 112, 114. The steady contact of the user's fingers with electrodes 112, 114 will produce a potential difference (i.e. voltage) therebetween.

At step 604, system 100 determines if a voltage is detected. If a voltage is detected, ECG signals are obtained from electrodes 112, 114 at step 606 to yield ECG data 124.

At step 608, any desired onboard processing of ECG data 124 is carried out.

At step 610, ECG signals 124 are stored in on-board data storage unit 120.

At step 612, remote ECG monitoring and data storage system 100 determines if it is paired with a receiving device 200. If system 100 is paired with a receiving device 200, then at step 614, system 100 initiates the transmission of ECG data 124 to receiving device 200 via wireless transceiver 130.

If at step 612 it is determined that system 100 is not paired with a receiving device 200, then system 100 returns to sleep mode 602, and wireless transceiver 130 is not activated. At a later time, a user can subsequently transfer stored ECG data 124 to a receiving device 200 by applying a predetermined tapping pattern of electrical contact to electrodes 112, 114. At step 616, system 100 determines via activation mechanism 132 whether the predetermined tapping pattern has been detected.

If the predetermined tapping pattern of electrical contact is detected at step 616, at step 618 system 100 pairs with receiving device 200 by activating wireless transceiver 130. At step 612, it is determined whether system 100 has successfully paired with receiving device 200. If system 100 has successfully paired with receiving device 200, at step 614, system 100 initiates the wireless transfer of stored ECG data 124 to receiving device 200 via wireless transceiver 130.

If at step 616, system 100 determines that the predetermined tapping pattern of electrical contact has not been applied to electrodes 112, 114, then system 100 returns to sleep mode 602 and wireless transceiver 130 is not activated.

Figure 17:
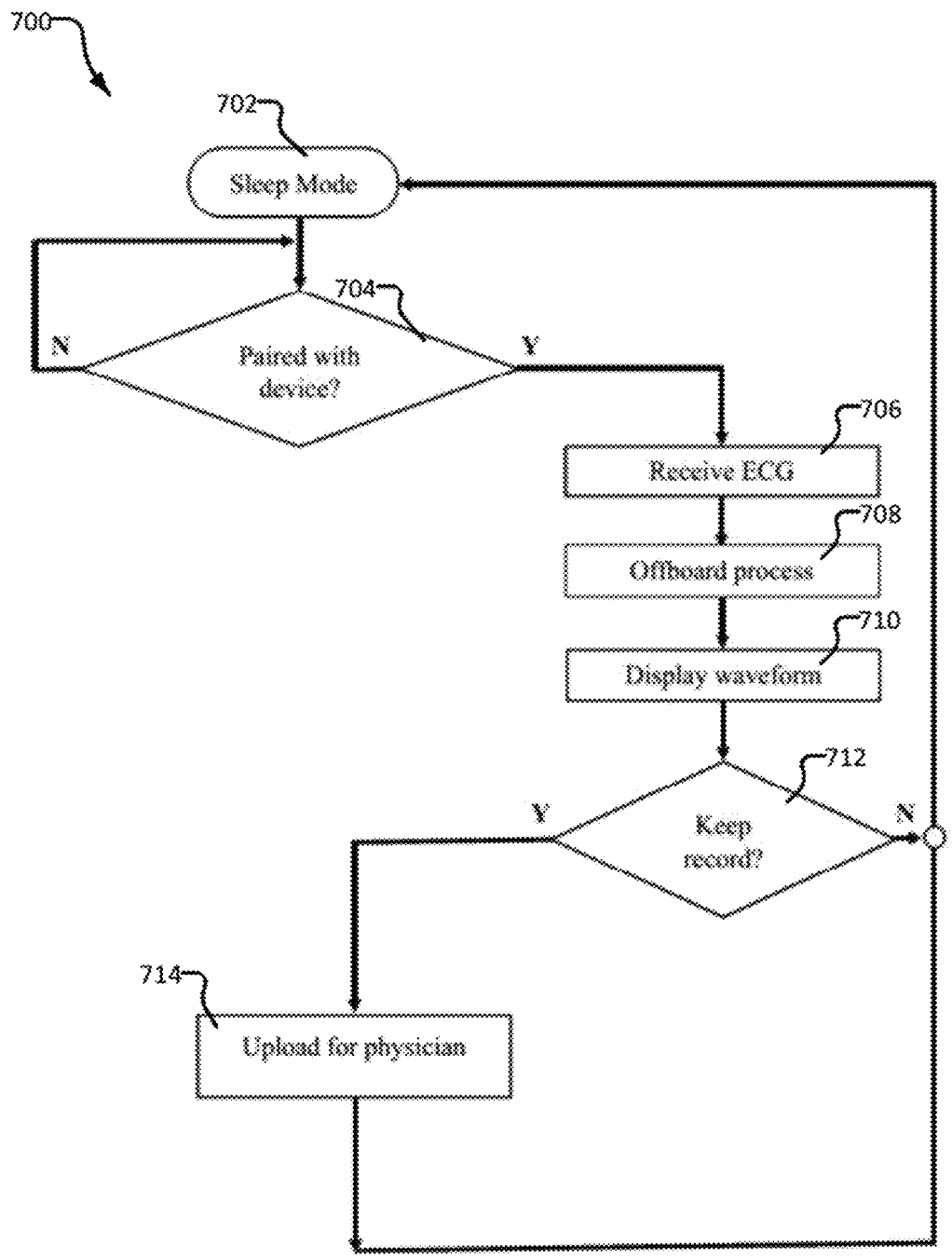
FIG. 17 shows a flow diagram of an example embodiment of transmitting ECG signals to a receiving device.

With reference to FIG. 17, an alternative embodiment of a method 700 of transmitting ECG data 124 to a receiving device 200 is illustrated. At step 702, system 100 is in sleep mode, i.e. system 100 is not transmitting wireless signals 126.

At step 704, system 100 determines whether it is paired with receiving device 200, i.e. whether it can exchange wireless signals 126 with receiving device 200. If system 100 is not paired with receiving device 200, it returns to sleep mode. If system 100 determines at step 704 that it is paired with receiving device 200, the method proceeds to step 706 and system 100 transmits ECG data 124, which is received by receiving device 200.

At step 708, any desired processing of ECG data 124 is carried out using receiving device 200. Because receiving device 200 is not subject to the same space constraints as system 100, greater levels of computing power and electrical power are available for receiving device 200, and ECG data 124 can be processed in more complex ways on receiving device 200 than is possible onboard system 100.

At step 710, receiving device 200 can display a waveform showing ECG data 124 to a user in a visually perceptible format.

At step 712, a user has the option to determine whether that particular record of ECG data 124 should be retained. If not, the record is deleted from on-board data storage unit 120 and system 100 returns to sleep mode. If the record is to be retained, at step 714, the user has the option to upload the record to a secure server for later review, for example by the user's physician.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

Without limitation, those skilled in the art will recognize that there are a number of different aspects of various embodiments of the present invention, including without limitation the following aspects:

1. A system for monitoring and recording ECG signals comprising:
   a housing defining a compartment;
   a pair of electrodes secured to the housing for obtaining ECG signals from a user;
   a processing unit positioned within the compartment for receiving the ECG signals;
   a data storage unit positioned within the compartment for storing data based on the ECG signals;
   a power storage unit positioned within the compartment for supplying power to the system; and
   a wireless communication unit positioned within the compartment for communicating the ECG signals or the data based on the ECG signals to a receiving device.
2. A system as defined in aspect 1, wherein the data storage unit comprises a circular memory.
3. A system as defined in aspect 2, wherein the data storage unit is adapted to provide an indication that the circular memory is full.
4. A system as defined in aspect 3, wherein the system is configured to receive an indication from a user to overwrite data in the circular memory when the circular memory is full.
5. A system as defined in aspect 4, wherein the indication from the user to overwrite data in the circular memory comprises continuing to maintain electrical contact with the electrodes for at least a predetermined period of time, and wherein the system is configured to sense the continued electrical contact with the electrodes for at least the predetermined period of time.
6. A system as defined in any one of aspects 1-5, further comprising a charging system for charging the power storage unit.
7. A system as defined in aspect 6, wherein the charging system comprises a mechanical energy harvesting system.
8. A system as defined in aspect 7, wherein the mechanical energy harvesting system comprises:
   a coil of wire;
   a magnet positioned for movement relative to the coil of wire, movement of the magnet relative to the coil of wire being caused by accelerative movements of a user; and
   a power rectifier circuit for feeding power to the power storage unit.
9. A system as defined in aspect 6, wherein the charging system comprises a capacitive charging system, and wherein the pair of electrodes is adapted to carry out capacitive charging.
10. A system as defined in any one of aspects 1-9, comprising an ultra-low power circuit positioned within the compartment, the ultra-low power circuit being configured to detect the application of a predefined tapping pattern of electrical contact on the pair of electrodes and to supply power to the wireless communication unit upon detection of the predefined tapping pattern of electrical contact.
11. A system as defined in aspect 10, wherein the ultra-low power circuit is configured to measure one of:
   electrical impedance between the pair of electrodes;
   an electrical voltage between the pair of electrodes; or
   saturation of a preamplifier stage
   in order to evaluate the predefined tapping pattern of electrical contact.
12. A system as defined in any one of aspects 1-11, wherein the data processing unit comprises a low-power microcontroller platform.
13. A system as defined in any one of aspects 1-12, wherein the electrodes comprise stainless steel, silver-silver chloride or polymer-based electrodes.
14. A system as defined in any one of aspects 1-13, wherein the electrodes comprise silver-silver chloride, and wherein the silver-silver chloride electrodes are recoatable.
15. A system as defined in any one of aspects 1-14, wherein the electrodes are detachable from the housing.
16. A system as defined in any one of aspects 1-15, wherein the electrodes are detachably mounted to the housing using a spring-loaded pin to secure the electrodes against a lip of the housing.
17. A system as defined in any one of aspects 1-16, wherein the wireless communication unit comprises a wireless transmitter and a wireless receiver.
18. A system as defined in any one of aspects 1-17, wherein the housing comprises an arm of a pair of eyeglasses.
19. A pair of eyeglasses for monitoring and recording ECG signals comprising:
   a first arm and a second arm;
   a compartment defined within the first arm;
   a pair of electrodes mounted to the first arm for obtaining ECG signals from a user;
   a processing unit positioned within the compartment for receiving the ECG signals;
   a data storage unit positioned within the compartment for storing the ECG signals;

a wireless communication unit positioned within the compartment for communicating the ECG signals to a receiving device; and a power storage unit positioned within the compartment for supplying power to the processing unit, the data storage unit, and the wireless communication unit.

20. A pair of eyeglasses for monitoring and recording ECG signals comprising:

a first arm and a second arm;

a first electrode mounted to the first arm and a second electrode mounted to the second arm for obtaining ECG signals from a user;

a processing unit positioned within the pair of eyeglasses for receiving the ECG signals;

a data storage unit positioned within the pair of eyeglasses for storing the ECG signals;

a wireless communication unit positioned within the pair of eyeglasses for communicating the ECG signals;

a power storage unit positioned within the pair of eyeglasses for supplying power to the processing unit, the data storage unit, and the wireless communication unit; and a neck strap extending between the first arm and the second arm, the neck strap providing electrical connectivity of components in the first arm with components in the second arm.

21. A method of acquiring ECG data using a remote ECG monitoring and data storage system comprising the steps of:

receiving ECG signals from a pair of electrodes when a finger from a first hand of a user is placed in contact with a first one of the pair of electrodes and a finger form a second hand of a user is placed in contact with a second one of the pair of electrodes;

processing the received ECG signals using an on-board processing unit provided within a compartment defined by a housing of the remote ECG monitoring and data storage system to yield ECG data; and storing the ECG data in a circular memory provided within the compartment.

22. A method as defined in aspect 21, wherein the step of processing the received ECG signals using the on-board processing unit comprises either or both of analog and digital signal processing.

23. A method as defined in any one of aspects 21-22, wherein the step of processing the received ECG signals using the on-board processing unit comprises:

analyzing the ECG signals in both the time and frequency domains to classify the type of ECG abnormality;

using a low pass filter to limit the system bandwidth; and/or using notch filtering to remove powerline interference picked up by the electrodes.

24. A method as defined in any one of aspects 21-23, wherein the step of processing the received ECG signals using the on-board processing unit comprises using a data compression scheme to compress the ECG data.

25. A method as defined in any one of aspects 21-24, further comprising transmitting ECG data to a receiving device using a wireless communications protocol.

26. A method as defined in aspect 25, wherein the step of transmitting ECG data to the receiving device is initiated by application of a predetermined tapping pattern of electrical contact on the electrodes.

27. A method as defined in any one of aspects 21-26, wherein the step of storing the ECG data in the circular memory comprises evaluating whether the circular memory is full and, if the circular memory is full, requesting an indication from a user to proceed before overwriting a record of ECG data previously stored in the circular memory.

28. A method as defined in aspect 27, wherein the indication from the user to proceed comprises application of a predetermined series of taps to an activation mechanism provided in the compartment, or wherein the indication from the user to proceed comprises a user continuing to maintain electrical contact with the electrodes for at least a predetermined period of time.

29. A method of using a remote ECG monitoring and data storage system comprising:

detaching a used pair of detachable sliver-sliver chloride electrodes from the remote ECG monitoring and data storage system; and installing a replacement pair of detachable silver-silver chloride electrodes on the remote ECG monitoring and data storage system.

30. A method as defined in aspect 29, wherein the step of installing the replacement pair of detachable silver-silver chloride electrodes comprises recoating the used pair of detachable silver-silver chloride electrodes to produce a recoated pair of detachable silver-silver chloride electrodes and installing the recoated pair of silver-silver chloride electrodes as the replacement pair of detachable silver-silver chloride electrodes.

31. A method as defined in any one of aspects 21-30, further comprising disposing of the used pair of detachable silver-silver chloride electrodes.

32. A method of using a remote ECG monitoring and data storage system comprising a pair of silver-silver chloride electrodes comprising recoating the silver-silver chloride electrodes in situ with a solution comprising chloride ions ($Cl^-$).

33. A method as defined in any one of aspects 21-32, wherein the remote ECG monitoring and data storage system provides a notification to a user when the silver-silver chloride electrodes require replacement or recoating.

The invention claimed is:

1. A system for monitoring and recording ECG signals comprising:

a housing defining a compartment that holds a plurality of electrodes, a processing unit, a data storage unit, a power storage unit, and a wireless transceiver unit that communicates with a paired external device;

said housing is portable and includes at least one of an independent use and a use with said paired external device;

said paired external device calculates an anticipated useful lifespan of said plurality of electrodes based on at least one of an age of an electrode, and the number of cycles of ECG data obtained by said electrode;

said plurality of electrodes includes at least two electrodes secured to the housing to obtain an ECG signals from a user and are coated in situ or replaced when the anticipated useful lifespan of electrodes is reached;

said processing unit receives the ECG signals from said electrodes by carrying out at least one of an analog processing, and a digital processing and analyzes the ECG signal to classify a type of ECG abnormality;

said ECG signal is compressed before being sent to said data storage unit, and is compressed and encrypted before sent to said wireless transceiver unit;

said data storage unit has a memory to store the EGC signal that is processed and compressed, and a recorded tapping pattern that includes at least one of a long tapping pattern, and a short tapping pattern;

said long tapping pattern is selected to be long enough that the wireless transceiver is not activated by spurious or random contact of a user's fingers with electrodes;

said short tapping pattern is selected to be short enough that said user can easily remember the stored tapping pattern and can execute the stored tapping pattern of electrical contact within a few seconds;

the recorded tapping pattern includes at least one of a predetermined pattern and an applied tapping pattern of electrical contact of the user's choosing;

said power storage unit supplies power to the system for monitoring and recording ECG signals and is recharged using at least one of a solar cell, a sound/ultrasound wave charger, and a body movement charger; and said wireless transceiver unit is activated by detecting said tapping pattern and then communicates with said paired external device and send at least one of a recorded EGC related information, and a real time ECG signal as it is obtained for further analysis and manipulation.

2. A system as defined in claim 1, wherein said housing defining a compartment is within at least one of a first arm, a second arm, and both arms of a pair of eyeglasses.

3. A system as defined in claim 1, wherein the data storage unit comprises a circular memory and is adapted to provide an indication that the circular memory is full.

4. A system as defined in claim 3, wherein the system is configured to receive an indication from a user to overwrite data in the circular memory when the circular memory is full.

5. A system as defined in claim 4, wherein the indication from the user to overwrite data in the circular memory comprises continuing to maintain electrical contact with the at least two electrodes for at least a predetermined period of time, and wherein the system is configured to sense the continued electrical contact with the at least two electrodes for at least the predetermined period of time.

6. A system as defined in claim 1, wherein said power storage unit is recharged using a microelectromechanical system (MEMS) using a piezoelectric material where piezoelectric material transforms mechanical strain energy, e.g. caused by vibrations, to electrical energy that is used to recharge the power storage unit.

7. A system as defined in claim 1, wherein the power storage unit is an ultracapacitor or a supercapacitor.

8. A system as defined in claim 1, comprising an ultra-low power circuit positioned within the compartment, the ultra-low power circuit being configured to measure one of:
  i. electrical impedance between the pair of electrodes;
  ii. an electrical voltage between the pair of electrodes; or
  iii. saturation of a preamplifier stage
  in order to evaluate the define electrical contact.

9. A system as defined in claim 1, wherein the at least two electrodes comprise at least one of stainless steel, a silver-silver chloride, and a polymer-based electrodes that are recoatable and detachable.

10. A system as defined in claim 1, wherein the surface of the electrodes is provided with a plurality of indentations to increase the surface area of the electrodes available for contact with fingers of a user and/or provide a tactile feedback sensation to a user, so that the user knows when his or her fingers are in contact with electrodes.

11. A system as defined in claim 1, wherein the paired external device comprises an application program and is at least one of a computer, a smart phone, a tablet and a wearable unit, wherein the wearable unit optionally comprises eyeglasses.

12. A system as defined in claim 1, wherein the application program provided on said paired external device calculates the anticipated expected lifetime of the electrodes and when the anticipated useful lifespan of the electrodes approaches, a user is given a warning signal by the application program to warn the user that electrodes should be replaced or recoated soon, wherein optionally the anticipated expected lifetime of the electrodes is calculated by evaluating the age of the electrodes and the number of cycles of ECG data obtained by electrodes.

13. A method of acquiring ECG data using a remote ECG monitoring and data storage system comprising the steps of:
  receiving ECG signals from at least two electrodes when a finger from a first hand of a user is placed in contact with a first one of the at least two electrodes and a finger from a second hand of a user is placed in contact with a second one of the at least two electrodes;
  processing the received ECG signals using an on-board processing unit provided within a compartment defined by a housing of the remote ECG monitoring and data storage system to yield ECG data;
  storing the ECG data in a data storage unit provided within the compartment;
  compressing the ECG data before storing in a data storage unit;
  compressing and encrypting the ECG data before sending to a wireless transceiver unit provided within the compartment;
  sending a compressed and encrypted ECG signal to a paired external device using the wireless transceiver;
  anticipating a useful lifespan of the electrodes by the paired external device using at least one of an age of the electrodes, and the number of cycles of ECG data obtained by the electrodes; and
  as an end of the anticipated useful lifespan of the electrodes approaches, providing a warning indication to a user to indicate that the end of the useful lifespan of the electrodes is approaching and that the electrodes should be replaced or recoated.

14. A method as defined in claim 13, wherein the step of processing the received ECG signals using the on-board processing unit comprises:
  analyzing the ECG signals in both the time and frequency domains;
  using a low pass filter to limit the system bandwidth; and/or
  using notch filtering to remove powerline interference picked up by the electrodes.

15. A method as defined claim 13 further comprising a step of transmitting the ECG data to a receiving device using a wireless transmission protocol, wherein the step of transmitting the ECG data to the receiving device is initiated by application of a predetermined long or short tapping pattern of electrical contact on the at least two electrodes.

16. A method as defined in claim 13, wherein the step of storing the ECG data in the storage unit comprises evaluating whether the storage unit is full and, if the storage unit is full, requesting an indication from a user to proceed before overwriting a record of ECG data previously stored in the storage unit.

17. A method as defined in claim 16, wherein the indication from the user to proceed comprises a user continuing to maintain electrical contact with the electrodes for at least a predetermined period of time.

* * * * *